United States Patent
Jackson et al.

(10) Patent No.: US 8,911,479 B2
(45) Date of Patent: Dec. 16, 2014

(54) MULTI-START CLOSURES FOR OPEN IMPLANTS

(71) Applicants: Roger P. Jackson, Prairie Village, KS (US); James L. Surber, Kansas City, KS (US)

(72) Inventors: Roger P. Jackson, Prairie Village, KS (US); James L. Surber, Kansas City, KS (US)

( * ) Notice: Subject to any disclaimer, the term of this patent is extended or adjusted under 35 U.S.C. 154(b) by 0 days.

(21) Appl. No.: 13/694,849

(22) Filed: Jan. 10, 2013

(65) Prior Publication Data

US 2013/0197585 A1 Aug. 1, 2013

Related U.S. Application Data

(60) Provisional application No. 61/631,746, filed on Jan. 10, 2012, provisional application No. 61/634,631, filed on Feb. 28, 2012.

(51) Int. Cl.
*A61B 17/70* (2006.01)

(52) U.S. Cl.
CPC ......... *A61B 17/7035* (2013.01); *A61B 17/7032* (2013.01)
USPC ....................................... 606/278

(58) Field of Classification Search
USPC ......... 606/246, 264–273, 275, 278, 279, 305, 606/306, 308, 315, 316; 403/362; 411/393
See application file for complete search history.

(56) References Cited

U.S. PATENT DOCUMENTS

| | | |
|---|---|---|
| 2,346,346 A | 4/1944 | Anderson |
| 2,362,999 A | 11/1944 | Elmer |
| 2,531,892 A | 11/1950 | Reese |
| 2,813,450 A | 11/1957 | Dzus |
| 3,013,244 A | 12/1961 | Rudy |
| 4,033,139 A | 7/1977 | Frederick |
| 4,759,672 A | 7/1988 | Nilsen et al. |
| 4,771,905 A | 9/1988 | Perne et al. |
| 4,790,297 A | 12/1988 | Luque |
| 4,946,458 A | 8/1990 | Harms et al. |
| 5,019,080 A | 5/1991 | Hemer |
| 5,129,388 A | 7/1992 | Vignaud et al. |
| 5,207,678 A | 5/1993 | Harms et al. |
| 5,261,912 A | 11/1993 | Frigg |
| 5,312,404 A | 5/1994 | Asher et al. |
| 5,360,431 A | 11/1994 | Puno et al. |
| 5,395,371 A | 3/1995 | Miller et al. |
| 5,429,639 A | 7/1995 | Judet |

(Continued)

FOREIGN PATENT DOCUMENTS

| | | |
|---|---|---|
| DE | 19507141 | 9/1996 |
| DE | 29903342 | 6/1999 |

(Continued)

OTHER PUBLICATIONS

*EBI Omega 21* Brochure, EBI Spine Systems, pub. 1999.

(Continued)

*Primary Examiner* — Pedro Philogene
*Assistant Examiner* — David Comstock
(74) *Attorney, Agent, or Firm* — John C. McMahon

(57) ABSTRACT

An open implant closure structure includes a helically wound guide and advancement structure having at least two helically wound forms thereon providing a multi-start closing mechanism for use between spaced arms of a cooperating open medical implant having mating helically wound structure thereon. Illustrated structures include interlocking flange forms, v-threads, square threads, reverse angle threads and buttress threads and receivers with break-off extensions and cooperating tooling.

22 Claims, 7 Drawing Sheets

(56) References Cited

U.S. PATENT DOCUMENTS

| | | |
|---|---|---|
| 5,443,467 A | 8/1995 | Biedermann et al. |
| 5,466,237 A | 11/1995 | Byrd, III et al. |
| 5,474,555 A | 12/1995 | Puno et al. |
| 5,476,462 A | 12/1995 | Allard et al. |
| 5,476,464 A | 12/1995 | Metz-Stavenhagen et al. |
| 5,496,321 A | 3/1996 | Puno et al. |
| 5,554,157 A | 9/1996 | Errico et al. |
| 5,569,247 A | 10/1996 | Morrison |
| 5,584,834 A | 12/1996 | Errico et al. |
| 5,586,984 A | 12/1996 | Errico et al. |
| 5,591,166 A | 1/1997 | Bernhardt et al. |
| 5,601,553 A | 2/1997 | Trebing et al. |
| 5,607,426 A | 3/1997 | Ralph et al. |
| 5,647,873 A | 7/1997 | Errico et al. |
| 5,669,911 A | 9/1997 | Errico et al. |
| 5,672,176 A | 9/1997 | Biedermann et al. |
| 5,681,319 A | 10/1997 | Biedermann et al. |
| 5,683,392 A | 11/1997 | Richelsoph |
| 5,690,630 A | 11/1997 | Errico et al. |
| 5,716,356 A | 2/1998 | Biedermann et al. |
| 5,725,528 A | 3/1998 | Errico et al. |
| 5,728,098 A | 3/1998 | Sherman et al. |
| 5,733,286 A | 3/1998 | Errico et al. |
| 5,738,685 A | 4/1998 | Halm et al. |
| 5,782,833 A | 7/1998 | Haider |
| 5,797,911 A | 8/1998 | Sherman et al. |
| 5,800,435 A | 9/1998 | Errico et al. |
| 5,817,094 A | 10/1998 | Errico et al. |
| 5,863,293 A | 1/1999 | Richelsoph |
| 5,873,878 A | 2/1999 | Harms et al. |
| 5,876,402 A | 3/1999 | Errico et al. |
| 5,879,350 A | 3/1999 | Sherman et al. |
| 5,879,351 A | 3/1999 | Viart |
| 5,882,350 A | 3/1999 | Ralph et al. |
| 5,885,286 A | 3/1999 | Sherman et al. |
| 5,891,145 A | 4/1999 | Morrison et al. |
| 5,938,663 A | 8/1999 | Petreto |
| 5,954,725 A | 9/1999 | Sherman et al. |
| 5,961,517 A | 10/1999 | Biedermann et al. |
| 5,964,760 A | 10/1999 | Richelsoph |
| 6,010,503 A | 1/2000 | Richelsoph et al. |
| 6,019,759 A | 2/2000 | Rogozinski |
| 6,022,350 A | 2/2000 | Ganem |
| 6,053,917 A | 4/2000 | Sherman et al. |
| 6,063,090 A | 5/2000 | Schlapfer |
| 6,074,391 A | 6/2000 | Metz-Stavenhagen et al. |
| 6,077,262 A | 6/2000 | Schlapfer et al. |
| 6,086,588 A | 7/2000 | Ameil et al. |
| 6,090,110 A | 7/2000 | Metz-Stavenhagen |
| 6,090,111 A | 7/2000 | Nichols |
| 6,099,528 A | 8/2000 | Saurat |
| 6,110,172 A | 8/2000 | Jackson |
| 6,113,601 A | 9/2000 | Tatar |
| 6,132,431 A | 10/2000 | Nilsson et al. |
| 6,132,432 A | 10/2000 | Richelsoph |
| 6,132,434 A | 10/2000 | Sherman et al. |
| 6,146,383 A | 11/2000 | Studer et al. |
| 6,183,472 B1 | 2/2001 | Lutz |
| 6,186,718 B1 | 2/2001 | Fogard |
| 6,187,005 B1 | 2/2001 | Brace et al. |
| 6,214,012 B1 | 4/2001 | Karpman et al. |
| RE37,161 E | 5/2001 | Michelson et al. |
| 6,224,596 B1 | 5/2001 | Jackson |
| 6,248,105 B1 | 6/2001 | Schlapfer et al. |
| 6,254,602 B1 | 7/2001 | Justis |
| 6,273,888 B1 | 8/2001 | Justis |
| 6,280,442 B1 | 8/2001 | Barker et al. |
| 6,280,445 B1 | 8/2001 | Morrison et al. |
| 6,287,308 B1 | 9/2001 | Betz et al. |
| 6,287,311 B1 | 9/2001 | Sherman et al. |
| 6,296,642 B1 | 10/2001 | Morrison et al. |
| 6,302,888 B1 | 10/2001 | Mellinger et al. |
| 6,309,391 B1 | 10/2001 | Crandall et al. |
| 6,331,179 B1 | 12/2001 | Freid et al. |
| 6,355,040 B1 | 3/2002 | Richelsoph et al. |
| RE37,665 E | 4/2002 | Ralph et al. |
| 6,368,321 B1 | 4/2002 | Jackson |
| 6,371,957 B1 | 4/2002 | Amrein et al. |
| 6,402,752 B2 | 6/2002 | Schaffler-Wachter et al. |
| 6,440,137 B1 | 8/2002 | Horvath et al. |
| 6,451,021 B1 | 9/2002 | Ralph et al. |
| 6,471,703 B1 | 10/2002 | Ashman |
| 6,471,705 B1 | 10/2002 | Biedermann et al. |
| 6,485,494 B1 | 11/2002 | Haider |
| 6,488,681 B2 | 12/2002 | Martin et al. |
| 6,508,818 B2 | 1/2003 | Steiner et al. |
| 6,520,962 B1 | 2/2003 | Taylor et al. |
| 6,527,804 B1 | 3/2003 | Gauchet et al. |
| 6,530,929 B1 | 3/2003 | Justis et al. |
| 6,533,786 B1 | 3/2003 | Needham et al. |
| 6,547,790 B2 | 4/2003 | Harkey, III et al. |
| 6,551,320 B2 | 4/2003 | Lieberman |
| 6,554,832 B2 | 4/2003 | Shluzas |
| 6,554,834 B1 | 4/2003 | Crozet et al. |
| 6,558,387 B2 | 5/2003 | Errico et al. |
| 6,562,040 B1 | 5/2003 | Wagner |
| 6,565,565 B1 | 5/2003 | Yuan et al. |
| 6,565,567 B1 | 5/2003 | Haider |
| 6,582,436 B2 | 6/2003 | Schlapfer et al. |
| 6,582,466 B1 | 6/2003 | Gauchet |
| 6,585,740 B2 | 7/2003 | Schlapfer et al. |
| 6,595,992 B1 | 7/2003 | Wagner et al. |
| 6,595,993 B2 | 7/2003 | Donno et al. |
| 6,610,063 B2 | 8/2003 | Kumar et al. |
| 6,613,050 B1 | 9/2003 | Wagner et al. |
| 6,623,485 B2 | 9/2003 | Doubler et al. |
| 6,626,907 B2 | 9/2003 | Campbell et al. |
| 6,626,908 B2 | 9/2003 | Cooper et al. |
| 6,635,059 B2 | 10/2003 | Randall et al. |
| 6,648,885 B1 | 11/2003 | Friesem |
| 6,648,887 B2 | 11/2003 | Ashman |
| 6,652,526 B1 | 11/2003 | Arafiles |
| 6,656,179 B1 | 12/2003 | Schaefer et al. |
| 6,656,181 B2 | 12/2003 | Dixon et al. |
| 6,660,004 B2 | 12/2003 | Barker et al. |
| 6,663,632 B1 | 12/2003 | Frigg |
| 6,663,635 B2 | 12/2003 | Frigg et al. |
| 6,673,073 B1 | 1/2004 | Schafer |
| 6,676,661 B1 | 1/2004 | Martin Benlloch et al. |
| 6,679,833 B2 | 1/2004 | Smith et al. |
| 6,682,529 B2 | 1/2004 | Stahurski |
| 6,689,133 B2 | 2/2004 | Morrison et al. |
| 6,689,134 B2 | 2/2004 | Ralph et al. |
| 6,695,843 B2 | 2/2004 | Biedermann et al. |
| 6,695,851 B2 | 2/2004 | Zdeblick et al. |
| 6,699,249 B2 | 3/2004 | Schlapfer et al. |
| 6,706,045 B2 | 3/2004 | Lin et al. |
| 6,712,818 B1 | 3/2004 | Michelson |
| 6,716,213 B2 | 4/2004 | Shitoto |
| 6,716,214 B1 | 4/2004 | Jackson |
| 6,716,247 B2 | 4/2004 | Michelson |
| 6,723,100 B2 | 4/2004 | Biedermann et al. |
| 6,726,689 B2 | 4/2004 | Jackson |
| 6,730,093 B2 | 5/2004 | Saint Martin |
| 6,730,127 B2 | 5/2004 | Michelson |
| 6,733,502 B2 | 5/2004 | Altarac et al. |
| 6,736,816 B2 | 5/2004 | Ritland |
| 6,736,820 B2 | 5/2004 | Biedermann et al. |
| 6,740,086 B2 | 5/2004 | Richelsoph |
| 6,746,449 B2 | 6/2004 | Jones et al. |
| 6,755,829 B1 | 6/2004 | Bono et al. |
| 6,755,835 B2 | 6/2004 | Schultheiss et al. |
| 6,755,836 B1 | 6/2004 | Lewis |
| 6,761,723 B2 | 7/2004 | Buttermann et al. |
| 6,767,351 B2 | 7/2004 | Orbay et al. |
| 6,770,075 B2 | 8/2004 | Howland |
| 6,780,186 B2 | 8/2004 | Errico et al. |
| 6,790,209 B2 | 9/2004 | Beale et al. |
| 6,827,719 B2 | 12/2004 | Ralph et al. |
| 6,830,571 B2 | 12/2004 | Lenke et al. |
| 6,835,196 B2 | 12/2004 | Biedermann et al. |
| 6,840,940 B2 | 1/2005 | Ralph et al. |
| 6,843,791 B2 | 1/2005 | Serhan |
| 6,858,031 B2 | 2/2005 | Morrison et al. |

(56) References Cited

U.S. PATENT DOCUMENTS

| | | |
|---|---|---|
| 6,869,432 B2 | 3/2005 | Schlapfer et al. |
| 6,869,433 B2 | 3/2005 | Glascott |
| 6,872,208 B1 | 3/2005 | McBride et al. |
| 6,896,677 B1 | 5/2005 | Lin |
| 6,932,817 B2 | 8/2005 | Baynham et al. |
| 6,945,972 B2 | 9/2005 | Frigg et al. |
| 6,953,462 B2 | 10/2005 | Lieberman |
| 6,955,677 B2 | 10/2005 | Dahners |
| 6,958,065 B2 | 10/2005 | Ueyama et al. |
| 6,964,664 B2 | 11/2005 | Freid et al. |
| 6,964,665 B2 | 11/2005 | Thomas et al. |
| 6,968,966 B2 | 11/2005 | Gregory |
| 6,974,460 B2 | 12/2005 | Carbone et al. |
| 6,979,334 B2 | 12/2005 | Dalton |
| 6,981,973 B2 | 1/2006 | McKinley |
| RE39,035 E | 3/2006 | Finn et al. |
| 7,008,228 B2 | 3/2006 | Bjorn et al. |
| 7,018,378 B2 | 3/2006 | Biedermann et al. |
| 7,018,379 B2 | 3/2006 | Drewry et al. |
| 7,022,122 B2 | 4/2006 | Amrein et al. |
| RE39,089 E | 5/2006 | Ralph et al. |
| 7,066,062 B2 | 6/2006 | Flesher |
| 7,066,937 B2 | 6/2006 | Shluzas |
| 7,081,116 B1 | 7/2006 | Carly |
| 7,083,621 B2 | 8/2006 | Shaolian et al. |
| 7,087,057 B2 | 8/2006 | Konieczynski et al. |
| 7,090,674 B2 | 8/2006 | Doubler et al. |
| 7,121,755 B2 | 10/2006 | Schlapfer et al. |
| 7,125,426 B2 | 10/2006 | Moumene et al. |
| 7,128,743 B2 | 10/2006 | Metz-Stavenhagen |
| 7,141,051 B2 | 11/2006 | Janowski et al. |
| 7,144,396 B2 | 12/2006 | Shluzas |
| 7,163,538 B2 | 1/2007 | Altarac et al. |
| 7,163,539 B2 | 1/2007 | Abdelgany et al. |
| 7,166,108 B2 | 1/2007 | Mazda et al. |
| 7,186,255 B2 | 3/2007 | Baynham et al. |
| 7,211,086 B2 | 5/2007 | Biedermann |
| 7,211,087 B2 | 5/2007 | Young |
| 7,214,227 B2 | 5/2007 | Colleran et al. |
| 7,223,268 B2 | 5/2007 | Biedermann |
| 7,264,621 B2 | 9/2007 | Coates et al. |
| 7,270,665 B2 | 9/2007 | Morrison et al. |
| 7,291,151 B2 | 11/2007 | Alvarez |
| 7,291,153 B2 | 11/2007 | Glascott |
| 7,294,127 B2 | 11/2007 | Leung et al. |
| 7,294,128 B2 | 11/2007 | Alleyne et al. |
| 7,294,129 B2 | 11/2007 | Hawkins et al. |
| 7,306,603 B2 | 12/2007 | Boehm, Jr. et al. |
| 7,306,604 B2 | 12/2007 | Carli |
| 7,306,606 B2 | 12/2007 | Sasing |
| 7,314,467 B2 | 1/2008 | Howland |
| 7,316,684 B1 | 1/2008 | Baccelli et al. |
| 7,322,979 B2 | 1/2008 | Crandall et al. |
| 7,335,201 B2 | 2/2008 | Doubler et al. |
| 7,335,202 B2 | 2/2008 | Matthis et al. |
| 7,338,490 B2 | 3/2008 | Ogilvie et al. |
| 7,338,491 B2 | 3/2008 | Baker et al. |
| 7,445,627 B2 | 11/2008 | Hawkes et al. |
| 7,476,228 B2 | 1/2009 | Abdou |
| 7,479,156 B2 | 1/2009 | Lourdel et al. |
| 7,491,218 B2 | 2/2009 | Landry et al. |
| 7,491,221 B2 | 2/2009 | David |
| 7,503,918 B2 | 3/2009 | Baccelli et al. |
| 7,503,924 B2 | 3/2009 | Lee et al. |
| 7,524,323 B2 | 4/2009 | Malandain |
| 7,527,640 B2 | 5/2009 | Ziolo et al. |
| 7,530,992 B2 | 5/2009 | Biedermann et al. |
| 7,559,943 B2 | 7/2009 | Mujwid |
| 7,563,264 B2 | 7/2009 | Landry et al. |
| 7,563,275 B2 | 7/2009 | Falahee et al. |
| 7,569,061 B2 | 8/2009 | Colleran |
| 7,572,279 B2 | 8/2009 | Jackson |
| 7,572,280 B2 | 8/2009 | Dickinson et al. |
| 7,575,587 B2 | 8/2009 | Rezach et al. |
| 7,582,107 B2 | 9/2009 | Trail et al. |
| 7,588,575 B2 | 9/2009 | Colleran et al. |
| 7,588,588 B2 | 9/2009 | Spitler et al. |
| 7,588,593 B2 | 9/2009 | Aferzon |
| 7,591,839 B2 | 9/2009 | Biedermann et al. |
| 7,601,166 B2 | 10/2009 | Biedermann et al. |
| 7,604,655 B2 | 10/2009 | Warnick |
| 7,604,656 B2 | 10/2009 | Shluzas |
| 7,611,518 B2 | 11/2009 | Walder et al. |
| 7,615,068 B2 | 11/2009 | Timm et al. |
| 7,621,941 B2 | 11/2009 | Schlapfer et al. |
| 7,625,394 B2 | 12/2009 | Molz, IV et al. |
| 7,641,674 B2 | 1/2010 | Young |
| 7,645,294 B2 | 1/2010 | Kalfas et al. |
| 7,648,522 B2 | 1/2010 | David |
| 7,674,277 B2 | 3/2010 | Burd et al. |
| 7,678,136 B2 | 3/2010 | Doubler et al. |
| 7,678,139 B2 | 3/2010 | Garamszegi et al. |
| 7,682,377 B2 | 3/2010 | Konieczynski et al. |
| 7,686,833 B1 | 3/2010 | Muhanna et al. |
| 7,686,834 B2 | 3/2010 | Saint Martin |
| 7,686,835 B2 | 3/2010 | Warnick |
| 7,691,129 B2 | 4/2010 | Felix |
| 7,691,131 B2 | 4/2010 | Graf |
| 7,691,132 B2 | 4/2010 | Landry et al. |
| 7,695,497 B2 | 4/2010 | Cordaro et al. |
| 7,695,498 B2 | 4/2010 | Ritland |
| 7,699,872 B2 | 4/2010 | Farris et al. |
| 7,699,875 B2 | 4/2010 | Timm |
| 7,699,876 B2 | 4/2010 | Barry et al. |
| 7,704,271 B2 | 4/2010 | Abdou |
| 7,713,288 B2 | 5/2010 | Timm et al. |
| 7,717,941 B2 | 5/2010 | Petit |
| 7,717,942 B2 | 5/2010 | Schumacher |
| 7,717,943 B2 | 5/2010 | Kirschman |
| 7,722,646 B2 | 5/2010 | Ralph et al. |
| 7,722,649 B2 | 5/2010 | Biedermann et al. |
| 7,722,651 B2 | 5/2010 | Kwak et al. |
| 7,722,652 B2 | 5/2010 | Justis et al. |
| 7,722,654 B2 | 5/2010 | Taylor et al. |
| 7,727,261 B2 | 6/2010 | Barker et al. |
| 7,731,736 B2 | 6/2010 | Guenther et al. |
| 7,731,749 B2 | 6/2010 | Biedermann et al. |
| 7,749,258 B2 | 7/2010 | Biedermann et al. |
| 7,758,618 B2 | 7/2010 | Walder et al. |
| 7,763,057 B2 | 7/2010 | Abdelgany et al. |
| 7,766,943 B1 | 8/2010 | Fallin et al. |
| 7,766,944 B2 | 8/2010 | Metz-Stavenhagen |
| 7,766,945 B2 | 8/2010 | Nilsson et al. |
| 7,766,946 B2 | 8/2010 | Bailly |
| 7,780,706 B2 | 8/2010 | Marino et al. |
| 7,785,351 B2 | 8/2010 | Gordon et al. |
| 7,785,354 B2 | 8/2010 | Biedermann et al. |
| 7,789,900 B2 | 9/2010 | Levy et al. |
| 7,794,477 B2 | 9/2010 | Melkent et al. |
| 7,794,480 B2 | 9/2010 | Gordon et al. |
| 7,806,913 B2 | 10/2010 | Fanger et al. |
| 7,811,288 B2 | 10/2010 | Jones et al. |
| 7,811,310 B2 | 10/2010 | Baker et al. |
| 7,819,902 B2 | 10/2010 | Abdelgany et al. |
| 7,878,351 B2 | 2/2011 | Falzoni et al. |
| RE42,545 E | 7/2011 | Ralph et al. |
| 7,972,364 B2 | 7/2011 | Biedermann et al. |
| 7,985,242 B2 | 7/2011 | Forton et al. |
| 7,985,248 B2 | 7/2011 | Walder et al. |
| RE42,626 E | 8/2011 | Taylor et al. |
| 7,988,694 B2 | 8/2011 | Barrus et al. |
| 7,988,711 B2 | 8/2011 | Erickson et al. |
| 8,002,806 B2 | 8/2011 | Justis |
| 8,012,183 B2 | 9/2011 | Alain |
| 8,012,186 B2 | 9/2011 | Pham et al. |
| 8,012,188 B2 | 9/2011 | Meltent et al. |
| 8,016,862 B2 | 9/2011 | Felix et al. |
| 8,016,866 B2 | 9/2011 | Warnick |
| 8,021,397 B2 | 9/2011 | Farris et al. |
| 8,025,681 B2 | 9/2011 | Colleran et al. |
| 8,029,539 B2 | 10/2011 | Kirschman |
| 8,034,084 B2 | 10/2011 | Landry et al. |
| 8,043,340 B1 | 10/2011 | Law |
| 8,048,124 B2 | 11/2011 | Chin et al. |

(56) References Cited

U.S. PATENT DOCUMENTS

| | | |
|---|---|---|
| 8,048,126 B2 | 11/2011 | Altarac et al. |
| 8,052,720 B2 | 11/2011 | Kuester et al. |
| 8,057,519 B2 | 11/2011 | Justis et al. |
| 8,062,339 B2 | 11/2011 | Hammer et al. |
| 8,066,744 B2 | 11/2011 | Justis et al. |
| 8,075,599 B2 | 12/2011 | Johnson et al. |
| 8,075,603 B2 | 12/2011 | Hammill, Sr. et al. |
| 8,083,776 B2 | 12/2011 | Alvarez |
| 8,100,946 B2 | 1/2012 | Strausbaugh et al. |
| 8,100,947 B2 | 1/2012 | Ensign et al. |
| 8,100,948 B2 | 1/2012 | Ensign et al. |
| 8,137,387 B2 | 3/2012 | Garamszegi |
| 8,162,990 B2 | 4/2012 | Potash et al. |
| 8,162,991 B2 | 4/2012 | Strauss et al. |
| 8,167,913 B2 | 5/2012 | Albert et al. |
| 8,167,914 B1 | 5/2012 | Hunt et al. |
| 8,197,517 B1 | 6/2012 | Lab et al. |
| 8,197,518 B2 | 6/2012 | Hammill, Sr. et al. |
| 8,221,471 B2 | 7/2012 | Kovach et al. |
| 8,221,472 B2 | 7/2012 | Peterson et al. |
| 8,236,032 B2 | 8/2012 | Ramsay et al. |
| 8,236,035 B1 | 8/2012 | Bedor |
| 2001/0001119 A1 | 5/2001 | Lombardo |
| 2002/0035366 A1 | 3/2002 | Walder et al. |
| 2002/0045898 A1 | 4/2002 | Freid et al. |
| 2002/0072751 A1 | 6/2002 | Jackson |
| 2002/0082602 A1 | 6/2002 | Biedermann et al. |
| 2002/0111626 A1 | 8/2002 | Ralph et al. |
| 2002/0133159 A1 | 9/2002 | Jackson |
| 2002/0143341 A1 | 10/2002 | Biedermann et al. |
| 2002/0173789 A1 | 11/2002 | Howland |
| 2002/0193795 A1 | 12/2002 | Gertzbein et al. |
| 2003/0023240 A1 | 1/2003 | Amrein et al. |
| 2003/0023243 A1 | 1/2003 | Biedermann et al. |
| 2003/0073996 A1 | 4/2003 | Doubler et al. |
| 2003/0093078 A1 | 5/2003 | Ritland |
| 2003/0100896 A1 | 5/2003 | Biedermann et al. |
| 2003/0105460 A1 | 6/2003 | Crandall et al. |
| 2003/0125741 A1 | 7/2003 | Biedermann et al. |
| 2003/0149432 A1 | 8/2003 | Frigg et al. |
| 2003/0153911 A1 | 8/2003 | Shluzas |
| 2003/0163133 A1 | 8/2003 | Altarac et al. |
| 2003/0176862 A1 | 9/2003 | Taylor et al. |
| 2003/0199873 A1 | 10/2003 | Richelsoph |
| 2003/0208204 A1 | 11/2003 | Bailey et al. |
| 2003/0216735 A1 | 11/2003 | Altarac et al. |
| 2004/0006342 A1 | 1/2004 | Altarac et al. |
| 2004/0092934 A1 | 5/2004 | Howland |
| 2004/0097933 A1 | 5/2004 | Lourdel et al. |
| 2004/0116929 A1 | 6/2004 | Barker et al. |
| 2004/0138662 A1 | 7/2004 | Landry et al. |
| 2004/0143265 A1 | 7/2004 | Landry et al. |
| 2004/0147929 A1 | 7/2004 | Biedermann et al. |
| 2004/0158247 A1 | 8/2004 | Sitiso et al. |
| 2004/0172022 A1 | 9/2004 | Landry et al. |
| 2004/0176766 A1 | 9/2004 | Shluzas |
| 2004/0186473 A1 | 9/2004 | Cournoyer et al. |
| 2004/0210216 A1 | 10/2004 | Farris et al. |
| 2004/0225289 A1 | 11/2004 | Biedermann et al. |
| 2004/0236330 A1 | 11/2004 | Purcell et al. |
| 2004/0249380 A1 | 12/2004 | Glascott |
| 2004/0267264 A1 | 12/2004 | Konieczynski et al. |
| 2005/0027296 A1 | 2/2005 | Thramann et al. |
| 2005/0055026 A1 | 3/2005 | Biedermann et al. |
| 2005/0070899 A1 | 3/2005 | Doubler et al. |
| 2005/0080415 A1 | 4/2005 | Keyer et al. |
| 2005/0096654 A1 | 5/2005 | Lin |
| 2005/0107788 A1 | 5/2005 | Beaurain et al. |
| 2005/0113927 A1 | 5/2005 | Malek |
| 2005/0131404 A1 | 6/2005 | Mazda et al. |
| 2005/0131413 A1 | 6/2005 | O'Driscoll et al. |
| 2005/0149023 A1 | 7/2005 | Ritland |
| 2005/0154389 A1 | 7/2005 | Selover et al. |
| 2005/0154391 A1 | 7/2005 | Doherty et al. |
| 2005/0159750 A1 | 7/2005 | Doherty |
| 2005/0165400 A1 | 7/2005 | Fernandez |
| 2005/0171540 A1 | 8/2005 | Lim et al. |
| 2005/0187548 A1 | 8/2005 | Butler et al. |
| 2005/0187555 A1 | 8/2005 | Biedermann et al. |
| 2005/0192580 A1 | 9/2005 | Dalton |
| 2005/0203511 A1 | 9/2005 | Wilson-MacDonald et al. |
| 2005/0203516 A1 | 9/2005 | Biedermann et al. |
| 2005/0216003 A1 | 9/2005 | Biedermann et al. |
| 2005/0228501 A1 | 10/2005 | Miller et al. |
| 2005/0234450 A1 | 10/2005 | Barker |
| 2005/0234451 A1 | 10/2005 | Markworth |
| 2005/0234452 A1 | 10/2005 | Malandain |
| 2005/0240181 A1 | 10/2005 | Boomer et al. |
| 2005/0240183 A1 | 10/2005 | Vaughan |
| 2005/0251137 A1 | 11/2005 | Ball |
| 2005/0251141 A1 | 11/2005 | Frigg et al. |
| 2005/0260058 A1 | 11/2005 | Casagne, III |
| 2005/0261687 A1 | 11/2005 | Garamszegi et al. |
| 2005/0267474 A1 | 12/2005 | Dalton |
| 2005/0273099 A1 | 12/2005 | Baccelli et al. |
| 2005/0273101 A1 | 12/2005 | Schumacher |
| 2005/0277919 A1 | 12/2005 | Slivka et al. |
| 2005/0277925 A1 | 12/2005 | Mujwid |
| 2005/0277928 A1 | 12/2005 | Boschert |
| 2005/0283152 A1 | 12/2005 | Lindemann et al. |
| 2005/0283157 A1 | 12/2005 | Coates et al. |
| 2005/0283238 A1 | 12/2005 | Reiley |
| 2005/0288669 A1 | 12/2005 | Abdou |
| 2005/0288671 A1 | 12/2005 | Yuan et al. |
| 2005/0288673 A1 | 12/2005 | Catbagan et al. |
| 2006/0004357 A1 | 1/2006 | Lee et al. |
| 2006/0004359 A1 | 1/2006 | Kramer et al. |
| 2006/0004360 A1 | 1/2006 | Kramer et al. |
| 2006/0004363 A1 | 1/2006 | Brockmeyer et al. |
| 2006/0009769 A1 | 1/2006 | Lieberman |
| 2006/0009770 A1 | 1/2006 | Speirs et al. |
| 2006/0015104 A1 | 1/2006 | Dalton |
| 2006/0025767 A1 | 2/2006 | Khalili |
| 2006/0025768 A1 | 2/2006 | Iott et al. |
| 2006/0025770 A1 | 2/2006 | Schlapfer et al. |
| 2006/0036242 A1 | 2/2006 | Nilsson et al. |
| 2006/0036252 A1 | 2/2006 | Baynham et al. |
| 2006/0052783 A1 | 3/2006 | Dant et al. |
| 2006/0052784 A1 | 3/2006 | Dant et al. |
| 2006/0052786 A1 | 3/2006 | Dant et al. |
| 2006/0058788 A1 | 3/2006 | Hammer et al. |
| 2006/0074419 A1 | 4/2006 | Taylor et al. |
| 2006/0079894 A1 | 4/2006 | Colleran et al. |
| 2006/0079895 A1 | 4/2006 | McLeer |
| 2006/0079899 A1 | 4/2006 | Ritland |
| 2006/0084981 A1 | 4/2006 | Shluzas |
| 2006/0084989 A1 | 4/2006 | Dickinson et al. |
| 2006/0084993 A1 | 4/2006 | Landry et al. |
| 2006/0084995 A1 | 4/2006 | Biedermann et al. |
| 2006/0089643 A1 | 4/2006 | Mujwid |
| 2006/0089644 A1 | 4/2006 | Felix |
| 2006/0095037 A1 | 5/2006 | Jones et al. |
| 2006/0106380 A1 | 5/2006 | Colleran et al. |
| 2006/0106383 A1 | 5/2006 | Biedermann et al. |
| 2006/0116677 A1 | 6/2006 | Burd et al. |
| 2006/0129147 A1 | 6/2006 | Biedermann et al. |
| 2006/0129149 A1 | 6/2006 | Iott et al. |
| 2006/0142761 A1 | 6/2006 | Landry et al. |
| 2006/0149232 A1 | 7/2006 | Sasing |
| 2006/0149241 A1 | 7/2006 | Richelsoph et al. |
| 2006/0149244 A1 | 7/2006 | Amrein et al. |
| 2006/0155277 A1 | 7/2006 | Metz-Stavenhagen |
| 2006/0155278 A1 | 7/2006 | Warnick |
| 2006/0161152 A1 | 7/2006 | Ensign et al. |
| 2006/0166535 A1 | 7/2006 | Brumfiled et al. |
| 2006/0167455 A1 | 7/2006 | Clement et al. |
| 2006/0173454 A1 | 8/2006 | Spitler et al. |
| 2006/0173456 A1 | 8/2006 | Hawkes et al. |
| 2006/0195098 A1 | 8/2006 | Schumacher |
| 2006/0200128 A1 | 9/2006 | Mueller |
| 2006/0200131 A1 | 9/2006 | Chao et al. |
| 2006/0200149 A1 | 9/2006 | Hoy et al. |
| 2006/0212034 A1 | 9/2006 | Triplett et al. |
| 2006/0217716 A1 | 9/2006 | Baker et al. |

(56) References Cited

U.S. PATENT DOCUMENTS

| | | |
|---|---|---|
| 2006/0229614 A1 | 10/2006 | Foley et al. |
| 2006/0229615 A1 | 10/2006 | Abdou |
| 2006/0235389 A1 | 10/2006 | Albert et al. |
| 2006/0235392 A1 | 10/2006 | Hammer et al. |
| 2006/0235393 A1 | 10/2006 | Bono et al. |
| 2006/0241593 A1 | 10/2006 | Sherman et al. |
| 2006/0241595 A1 | 10/2006 | Molz, IV et al. |
| 2006/0241599 A1 | 10/2006 | Konieczynski et al. |
| 2006/0241600 A1 | 10/2006 | Ensign et al. |
| 2006/0247624 A1 | 11/2006 | Banouskou et al. |
| 2006/0247631 A1 | 11/2006 | Ahn et al. |
| 2006/0247636 A1 | 11/2006 | Yuan et al. |
| 2006/0247779 A1 | 11/2006 | Gordon et al. |
| 2006/0264933 A1 | 11/2006 | Baker et al. |
| 2006/0264936 A1 | 11/2006 | Partin et al. |
| 2006/0276787 A1 | 12/2006 | Zubok et al. |
| 2006/0276789 A1 | 12/2006 | Jackson |
| 2006/0276791 A1 | 12/2006 | Shluzas |
| 2006/0276792 A1 | 12/2006 | Ensign et al. |
| 2006/0282074 A1 | 12/2006 | Renaud et al. |
| 2006/0293659 A1 | 12/2006 | Alvarez |
| 2006/0293665 A1 | 12/2006 | Shluzas |
| 2006/0293666 A1 | 12/2006 | Matthis et al. |
| 2007/0016188 A1 | 1/2007 | Boehm, Jr. et al. |
| 2007/0016198 A1 | 1/2007 | Boehm, Jr. et al. |
| 2007/0021750 A1 | 1/2007 | Shluzas et al. |
| 2007/0043355 A1 | 2/2007 | Bette et al. |
| 2007/0043357 A1 | 2/2007 | Kirschman |
| 2007/0043358 A1 | 2/2007 | Molz, IV et al. |
| 2007/0043359 A1 | 2/2007 | Altarac et al. |
| 2007/0043364 A1 | 2/2007 | Cawley et al. |
| 2007/0049933 A1 | 3/2007 | Ahn et al. |
| 2007/0055235 A1 | 3/2007 | Janowski et al. |
| 2007/0055238 A1 | 3/2007 | Biedermann et al. |
| 2007/0055239 A1 | 3/2007 | Sweeney et al. |
| 2007/0055240 A1 | 3/2007 | Matthis et al. |
| 2007/0055241 A1 | 3/2007 | Matthis et al. |
| 2007/0055242 A1 | 3/2007 | Bailly |
| 2007/0055244 A1 | 3/2007 | Jackson |
| 2007/0073291 A1 | 3/2007 | Cordaro et al. |
| 2007/0078460 A1 | 4/2007 | Frigg et al. |
| 2007/0083199 A1 | 4/2007 | Baccelli |
| 2007/0088357 A1 | 4/2007 | Johnson et al. |
| 2007/0093817 A1 | 4/2007 | Barrus et al. |
| 2007/0093818 A1 | 4/2007 | Biedermann et al. |
| 2007/0093819 A1 | 4/2007 | Albert |
| 2007/0093826 A1 | 4/2007 | Hawkes et al. |
| 2007/0093827 A1 | 4/2007 | Warnick |
| 2007/0093831 A1 | 4/2007 | Abdelgany et al. |
| 2007/0100341 A1 | 5/2007 | Reglos et al. |
| 2007/0118117 A1 | 5/2007 | Altarac et al. |
| 2007/0118118 A1 | 5/2007 | Kwak et al. |
| 2007/0118123 A1 | 5/2007 | Strausbaugh et al. |
| 2007/0118124 A1 | 5/2007 | Biedermann et al. |
| 2007/0123862 A1 | 5/2007 | Warnick |
| 2007/0123864 A1 | 5/2007 | Walder et al. |
| 2007/0123867 A1 | 5/2007 | Kirschman |
| 2007/0123870 A1 | 5/2007 | Jeon et al. |
| 2007/0161986 A1 | 7/2007 | Levy |
| 2007/0161994 A1 | 7/2007 | Lowery et al. |
| 2007/0161995 A1 | 7/2007 | Trautwein et al. |
| 2007/0161996 A1 | 7/2007 | Biedermann et al. |
| 2007/0161999 A1 | 7/2007 | Biedermann et al. |
| 2007/0167948 A1 | 7/2007 | Abdou |
| 2007/0167949 A1 | 7/2007 | Altarac et al. |
| 2007/0173819 A1 | 7/2007 | Sandlin |
| 2007/0173820 A1 | 7/2007 | Trieu |
| 2007/0173828 A1 | 7/2007 | Firkins et al. |
| 2007/0191839 A1 | 8/2007 | Justis et al. |
| 2007/0198014 A1 | 8/2007 | Graf et al. |
| 2007/0208344 A1 | 9/2007 | Young |
| 2007/0225707 A1 | 9/2007 | Wisnewski et al. |
| 2007/0225711 A1 | 9/2007 | Ensign |
| 2007/0233078 A1 | 10/2007 | Justis et al. |
| 2007/0233080 A1 | 10/2007 | Na et al. |
| 2007/0233086 A1 | 10/2007 | Harms et al. |
| 2007/0233087 A1 | 10/2007 | Schlapfer |
| 2007/0250061 A1 | 10/2007 | Chin et al. |
| 2007/0260246 A1 | 11/2007 | Biedermann |
| 2007/0270806 A1 | 11/2007 | Foley et al. |
| 2007/0270807 A1 | 11/2007 | Armstrong et al. |
| 2007/0270810 A1 | 11/2007 | Sanders |
| 2007/0270813 A1 | 11/2007 | Garamszegi |
| 2007/0270815 A1 | 11/2007 | Johnson et al. |
| 2007/0270830 A1 | 11/2007 | Morrison |
| 2007/0270831 A1 | 11/2007 | Dewey et al. |
| 2007/0270832 A1 | 11/2007 | Moore |
| 2007/0270835 A1 | 11/2007 | Wisnewski |
| 2007/0270839 A1 | 11/2007 | Jeon et al. |
| 2007/0288004 A1 | 12/2007 | Alvarez |
| 2008/0009862 A1 | 1/2008 | Hoffman |
| 2008/0009864 A1 | 1/2008 | Forton et al. |
| 2008/0015578 A1 | 1/2008 | Erickson et al. |
| 2008/0015579 A1 | 1/2008 | Whipple |
| 2008/0015580 A1 | 1/2008 | Chao |
| 2008/0015584 A1 | 1/2008 | Richelsoph |
| 2008/0015586 A1 | 1/2008 | Krishna et al. |
| 2008/0021454 A1 | 1/2008 | Chao et al. |
| 2008/0021455 A1 | 1/2008 | Chao et al. |
| 2008/0021462 A1 | 1/2008 | Trieu |
| 2008/0021464 A1 | 1/2008 | Morin et al. |
| 2008/0021473 A1 | 1/2008 | Butler et al. |
| 2008/0027432 A1 | 1/2008 | Strauss et al. |
| 2008/0039838 A1 | 2/2008 | Landry et al. |
| 2008/0039843 A1 | 2/2008 | Abdou |
| 2008/0045951 A1 | 2/2008 | Fanger et al. |
| 2008/0045955 A1 | 2/2008 | Berrevoets et al. |
| 2008/0045957 A1 | 2/2008 | Landry et al. |
| 2008/0051780 A1 | 2/2008 | Vaidya et al. |
| 2008/0058811 A1 | 3/2008 | Alleyne et al. |
| 2008/0058812 A1 | 3/2008 | Zehnder |
| 2008/0065073 A1 | 3/2008 | Perriello et al. |
| 2008/0065075 A1 | 3/2008 | Dant |
| 2008/0065077 A1 | 3/2008 | Ferree |
| 2008/0071273 A1 | 3/2008 | Hawkes et al. |
| 2008/0071274 A1 | 3/2008 | Ensign |
| 2008/0071277 A1 | 3/2008 | Warnick |
| 2008/0077139 A1 | 3/2008 | Landry et al. |
| 2008/0086131 A1 | 4/2008 | Daly et al. |
| 2008/0086132 A1 | 4/2008 | Biedermann et al. |
| 2008/0097441 A1 | 4/2008 | Hayes et al. |
| 2008/0097457 A1 | 4/2008 | Warnick |
| 2008/0108992 A1 | 5/2008 | Barry et al. |
| 2008/0119858 A1 | 5/2008 | Potash |
| 2008/0140075 A1 | 6/2008 | Ensign et al. |
| 2008/0154315 A1 | 6/2008 | Jackson |
| 2008/0161859 A1 | 7/2008 | Nilsson |
| 2008/0161863 A1 | 7/2008 | Arnold et al. |
| 2008/0177321 A1 | 7/2008 | Drewry et al. |
| 2008/0177322 A1 | 7/2008 | Davis et al. |
| 2008/0177332 A1 | 7/2008 | Reiley et al. |
| 2008/0183215 A1 | 7/2008 | Altarac et al. |
| 2008/0183223 A1 | 7/2008 | Jeon et al. |
| 2008/0195159 A1 | 8/2008 | Kloss et al. |
| 2008/0200956 A1 | 8/2008 | Beckwith et al. |
| 2008/0215095 A1 | 9/2008 | Biedermann et al. |
| 2008/0228229 A1 | 9/2008 | Walder et al. |
| 2008/0234734 A1 | 9/2008 | Walder et al. |
| 2008/0234756 A1 | 9/2008 | Sutcliffe et al. |
| 2008/0234759 A1 | 9/2008 | Marino |
| 2008/0249570 A1 | 10/2008 | Carson et al. |
| 2008/0249576 A1 | 10/2008 | Wawkes et al. |
| 2008/0262548 A1 | 10/2008 | Lange et al. |
| 2008/0262556 A1 | 10/2008 | Jacofsky et al. |
| 2008/0269742 A1 | 10/2008 | Levy et al. |
| 2008/0269809 A1 | 10/2008 | Garamszegi |
| 2008/0287994 A1 | 11/2008 | Perez-Cruet et al. |
| 2008/0288002 A1 | 11/2008 | Crall et al. |
| 2008/0306528 A1 | 12/2008 | Winslow et al. |
| 2008/0306533 A1 | 12/2008 | Winslow et al. |
| 2008/0306539 A1 | 12/2008 | Cain et al. |
| 2008/0312655 A1 | 12/2008 | Kirschman et al. |
| 2008/0312692 A1 | 12/2008 | Brennan et al. |
| 2008/0312696 A1 | 12/2008 | Batters et al. |

(56) References Cited

U.S. PATENT DOCUMENTS

| | | |
|---|---|---|
| 2008/0312701 A1 | 12/2008 | Batters et al. |
| 2009/0005787 A1 | 1/2009 | Crall et al. |
| 2009/0005813 A1 | 1/2009 | Crall et al. |
| 2009/0005814 A1 | 1/2009 | Miller et al. |
| 2009/0012567 A1 | 1/2009 | Biedermann et al. |
| 2009/0018591 A1 | 1/2009 | Hawkes et al. |
| 2009/0024169 A1 | 1/2009 | Triplett et al. |
| 2009/0030457 A1 | 1/2009 | Janowski et al. |
| 2009/0036929 A1 | 2/2009 | Reglos et al. |
| 2009/0036932 A1 | 2/2009 | Rouyer et al. |
| 2009/0036934 A1 | 2/2009 | Biedermann et al. |
| 2009/0062860 A1 | 3/2009 | Frasier et al. |
| 2009/0062865 A1 | 3/2009 | Schumacher |
| 2009/0062867 A1 | 3/2009 | Schumacher |
| 2009/0062914 A1 | 3/2009 | Marino |
| 2009/0069849 A1 | 3/2009 | Oh et al. |
| 2009/0069852 A1 | 3/2009 | Farris et al. |
| 2009/0069853 A1 | 3/2009 | Schumacher |
| 2009/0076550 A1 | 3/2009 | Bernhardt, Jr. et al. |
| 2009/0076552 A1 | 3/2009 | Tornier |
| 2009/0082809 A1 | 3/2009 | Nguyen et al. |
| 2009/0082812 A1 | 3/2009 | Lewis |
| 2009/0082815 A1 | 3/2009 | Zylber et al. |
| 2009/0082819 A1 | 3/2009 | Blain et al. |
| 2009/0088799 A1 | 4/2009 | Yeh |
| 2009/0088807 A1 | 4/2009 | Castaneda et al. |
| 2009/0093843 A1 | 4/2009 | Lemoine et al. |
| 2009/0105769 A1 | 4/2009 | Rock et al. |
| 2009/0105770 A1 | 4/2009 | Berrevoets et al. |
| 2009/0105771 A1 | 4/2009 | Lei et al. |
| 2009/0118772 A1 | 5/2009 | Diederich et al. |
| 2009/0131983 A1 | 5/2009 | Biedermann |
| 2009/0138044 A1 | 5/2009 | Bergeron et al. |
| 2009/0138052 A1 | 5/2009 | Biedermann et al. |
| 2009/0143827 A1 | 6/2009 | Levy et al. |
| 2009/0143829 A1 | 6/2009 | Shluzas |
| 2009/0149887 A1 | 6/2009 | Schlaepfer et al. |
| 2009/0163955 A1 | 6/2009 | Moumene et al. |
| 2009/0163956 A1 | 6/2009 | Biedermann et al. |
| 2009/0163961 A1 | 6/2009 | Kirschman |
| 2009/0163963 A1 | 6/2009 | Berrevoets |
| 2009/0182380 A1 | 7/2009 | Abdelgany |
| 2009/0192548 A1 | 7/2009 | Jeon et al. |
| 2009/0192551 A1 | 7/2009 | Cianfrani et al. |
| 2009/0198280 A1 | 8/2009 | Spratt et al. |
| 2009/0198289 A1 | 8/2009 | Manderson |
| 2009/0198291 A1 | 8/2009 | Kevin et al. |
| 2009/0204155 A1 | 8/2009 | Aschmann |
| 2009/0216280 A1 | 8/2009 | Hutchinson |
| 2009/0248030 A1 | 10/2009 | Butler et al. |
| 2009/0248075 A1 | 10/2009 | Ogilvie et al. |
| 2009/0248088 A1 | 10/2009 | Biedermann |
| 2009/0254125 A1 | 10/2009 | Predick |
| 2009/0259254 A1 | 10/2009 | Pisharodi |
| 2009/0264896 A1 | 10/2009 | Biedermann et al. |
| 2009/0264933 A1 | 10/2009 | Carls et al. |
| 2009/0270916 A1 | 10/2009 | Ramsay et al. |
| 2009/0270917 A1 | 10/2009 | Boehm |
| 2009/0281571 A1 | 11/2009 | Weaver et al. |
| 2009/0281572 A1 | 11/2009 | White |
| 2009/0281573 A1 | 11/2009 | Biedermann et al. |
| 2009/0287253 A1 | 11/2009 | Felix et al. |
| 2009/0299415 A1 | 12/2009 | Pimenta |
| 2009/0306719 A1 | 12/2009 | Meyer, III et al. |
| 2009/0306720 A1 | 12/2009 | Doubler et al. |
| 2009/0312804 A1 | 12/2009 | Gamache et al. |
| 2009/0326582 A1 | 12/2009 | Songer et al. |
| 2009/0326587 A1 | 12/2009 | Matthis et al. |
| 2010/0004692 A1 | 1/2010 | Biedermann et al. |
| 2010/0010540 A1 | 1/2010 | Park |
| 2010/0016898 A1 | 1/2010 | Shluzas |
| 2010/0057125 A1 | 3/2010 | Viker |
| 2010/0057126 A1 | 3/2010 | Hestad |
| 2010/0063545 A1 | 3/2010 | Richelsoph |
| 2010/0063546 A1 | 3/2010 | Miller et al. |
| 2010/0063550 A1 | 3/2010 | Felix et al. |
| 2010/0063551 A1 | 3/2010 | Richelsoph |
| 2010/0063553 A1 | 3/2010 | Warnick |
| 2010/0069963 A1 | 3/2010 | Eckman |
| 2010/0069969 A1 | 3/2010 | Ampuero et al. |
| 2010/0087861 A1 | 4/2010 | Lechmann et al. |
| 2010/0087865 A1 | 4/2010 | Biedermann et al. |
| 2010/0094343 A1 | 4/2010 | Pham et al. |
| 2010/0094345 A1 | 4/2010 | Saidha et al. |
| 2010/0094348 A1 | 4/2010 | Biedermann et al. |
| 2010/0094349 A1 | 4/2010 | Hammer et al. |
| 2010/0094352 A1 | 4/2010 | Iott et al. |
| 2010/0094353 A1 | 4/2010 | Shim et al. |
| 2010/0100136 A1 | 4/2010 | Won et al. |
| 2010/0100137 A1 | 4/2010 | Justis et al. |
| 2010/0106189 A1 | 4/2010 | Miller |
| 2010/0114170 A1 | 5/2010 | Barrus et al. |
| 2010/0114171 A1 | 5/2010 | Boachie-Adjei et al. |
| 2010/0114180 A1 | 5/2010 | Rock et al. |
| 2010/0125302 A1 | 5/2010 | Hammill, Sr. et al. |
| 2010/0131017 A1 | 5/2010 | Farris et al. |
| 2010/0131018 A1 | 5/2010 | Konieczynski et al. |
| 2010/0137918 A1 | 6/2010 | Wilcox et al. |
| 2010/0137920 A1 | 6/2010 | Hammill, Sr. et al. |
| 2010/0145390 A1 | 6/2010 | McCarthy et al. |
| 2010/0152776 A1 | 6/2010 | Keyer et al. |
| 2010/0152785 A1 | 6/2010 | Forton et al. |
| 2010/0152787 A1 | 6/2010 | Walsh et al. |
| 2010/0152788 A1 | 6/2010 | Warnick |
| 2010/0160965 A1 | 6/2010 | Viker |
| 2010/0160974 A1 | 6/2010 | Viker |
| 2010/0160980 A1 | 6/2010 | Walsh et al. |
| 2010/0168796 A1 | 7/2010 | Eliasen et al. |
| 2010/0168800 A1 | 7/2010 | Biedermann et al. |
| 2010/0168801 A1 | 7/2010 | Biedermann et al. |
| 2010/0174322 A1 | 7/2010 | Abdelgany et al. |
| 2010/0179603 A1 | 7/2010 | Warnick |
| 2010/0185247 A1 | 7/2010 | Richelsoph |
| 2010/0191290 A1 | 7/2010 | Felix |
| 2010/0198269 A1 | 8/2010 | Taylor et al. |
| 2010/0198270 A1 | 8/2010 | Barker et al. |
| 2010/0198272 A1 | 8/2010 | Keyer et al. |
| 2010/0204735 A1 | 8/2010 | Gephart et al. |
| 2010/0222822 A1 | 9/2010 | Farris et al. |
| 2010/0228293 A1 | 9/2010 | Courtney et al. |
| 2010/0234891 A1 | 9/2010 | Freeman et al. |
| 2010/0241170 A1 | 9/2010 | Cammisa et al. |
| 2010/0249846 A1 | 9/2010 | Simonson |
| 2010/0249856 A1 | 9/2010 | Iott et al. |
| 2010/0256681 A1 | 10/2010 | Hammer et al. |
| 2010/0256682 A1 | 10/2010 | Fallin et al. |
| 2010/0262196 A1 | 10/2010 | Barrus et al. |
| 2011/0166606 A1 | 7/2011 | Stihl et al. |
| 2011/0172715 A1 | 7/2011 | Pond, Jr. et al. |
| 2011/0178558 A1 | 7/2011 | Barry |
| 2011/0184471 A1 | 7/2011 | Foley et al. |
| 2011/0190822 A1 | 8/2011 | Spitler et al. |
| 2011/0190823 A1 | 8/2011 | Bergeron et al. |
| 2011/0190826 A1 | 8/2011 | Ogilvie et al. |
| 2011/0196427 A1 | 8/2011 | Trautwein et al. |
| 2011/0202095 A1 | 8/2011 | Semler et al. |
| 2011/0208251 A1 | 8/2011 | Hammill, Sr. et al. |
| 2011/0230917 A1 | 9/2011 | Carson et al. |
| 2011/0251644 A1 | 10/2011 | Hestad et al. |
| 2011/0257687 A1 | 10/2011 | Trieu et al. |
| 2011/0257689 A1 | 10/2011 | Fiechter et al. |
| 2011/0257690 A1 | 10/2011 | Rezach |

FOREIGN PATENT DOCUMENTS

| | | |
|---|---|---|
| EP | 1121902 | 8/2001 |
| EP | 1190678 | 3/2002 |
| EP | 1210914 | 6/2002 |
| EP | 1570795 | 9/2005 |
| EP | 1579816 | 9/2005 |
| EP | 1634537 | 3/2006 |
| EP | 1925263 | 5/2008 |
| EP | 2380513 | 10/2011 |
| FR | 2729291 | 7/1996 |

(56) References Cited

FOREIGN PATENT DOCUMENTS

| | | |
|---|---|---|
| FR | 2796545 | 1/2001 |
| FR | 2856578 | 6/2003 |
| FR | 2865373 | 1/2004 |
| FR | 2865375 | 1/2004 |
| FR | 2865377 | 1/2004 |
| FR | 2857850 | 4/2004 |
| FR | 2865378 | 10/2004 |
| FR | 2925288 | 6/2009 |
| GB | 9202745.8 | 4/1992 |
| GB | 2365345 | 2/2002 |
| WO | WO95/01132 | 1/1995 |
| WO | WO01/10317 | 2/2001 |
| WO | WO02/054966 | 7/2002 |
| WO | WO03/068088 | 8/2003 |
| WO | WO2004/041100 | 5/2004 |
| WO | WO2004/089245 | 10/2004 |
| WO | WO2004/107997 | 12/2004 |
| WO | WO2005/000136 | 1/2005 |
| WO | WO2005/000137 | 1/2005 |
| WO | WO2005/020829 | 3/2005 |
| WO | WO2005/072632 | 8/2005 |
| WO | WO2005/082262 | 9/2005 |
| WO | WO2005/099400 | 10/2005 |
| WO | WO2006/005198 | 1/2006 |
| WO | WO2006/012088 | 2/2006 |
| WO | WO2006/017616 | 2/2006 |
| WO | WO2006/028537 | 3/2006 |
| WO | WO2006/119241 | 11/2006 |
| WO | WO2007/118045 | 10/2007 |
| WO | WO2007/124222 | 11/2007 |
| WO | WO2007/130835 | 11/2007 |
| WO | WO2007/130840 | 11/2007 |
| WO | WO2007/130941 | 11/2007 |
| WO | WO2008/088731 | 7/2008 |
| WO | WO2009/015100 | 1/2009 |
| WO | WO2012/075827 | 6/2012 |
| WO | WO2012/088890 | 7/2012 |

OTHER PUBLICATIONS

*Claris Instrumentation* Brochure, G Med, pub. 1997.
*VLS System Variable Locking Screw* Brochure, Interpore Cross International, 1999.
*CD Horizon M8 Multi Axial Screw Spinal System* Brochure, Medtronic Sofamor Danek, no publish date.
*Contour Spinal System* Brochure, Ortho Development, no publish date.
*Xia Spinal System* Brochure, Stryker Howmedica Osteonics, no publish date.
*The Rod Plate System* Brochure, Stryker Howmedica Osteonics, pub. Oct. 1999.
*Silhouette Spinal Fixation System* Brochure, Sulzer Medica Spine-Tech, no publish date.
*SDRS Surgical Dynamics Rod System* Brochure, Surgical Dynamics, pub. 1998-1999.
*Versalok Low Back Fixation System* Brochure, Wright Medical Technology, Inc., pub. 1997.
*The Strength of Innovation* Advertisement, Blackstone Medical Inc., no publish date.
*The Moss Miami 6.0mm System* Advertisement, author unknown, no publish date.

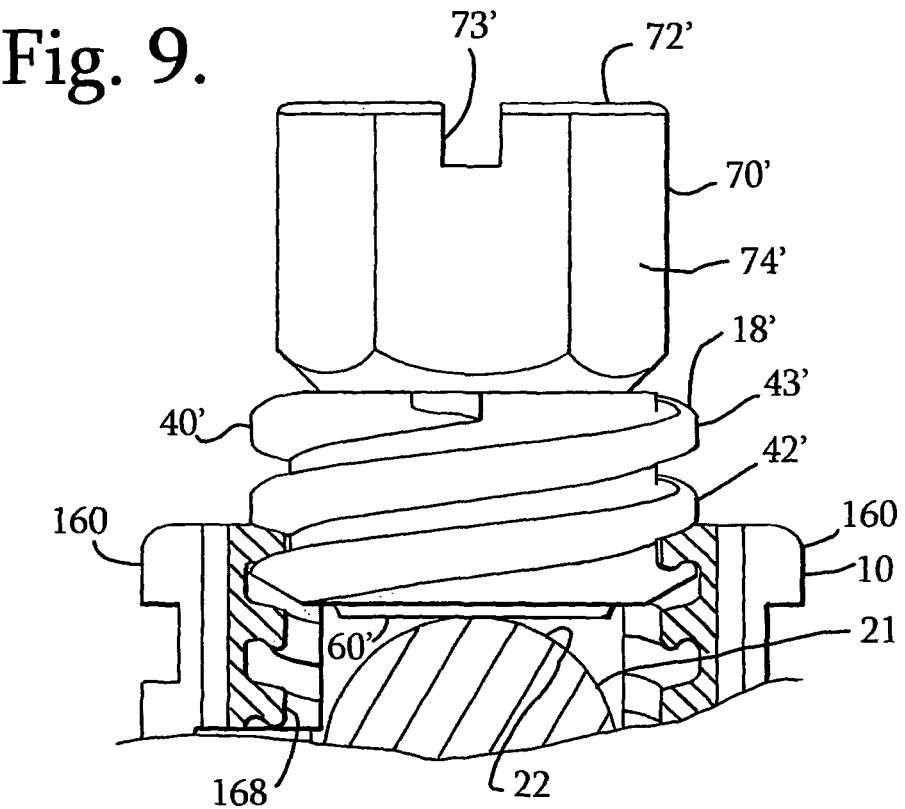
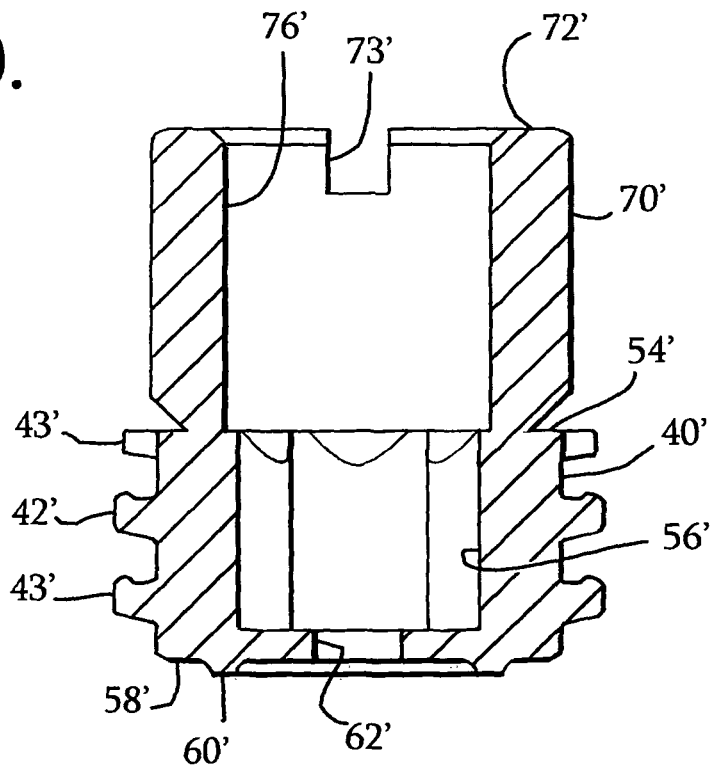

Fig. 15.
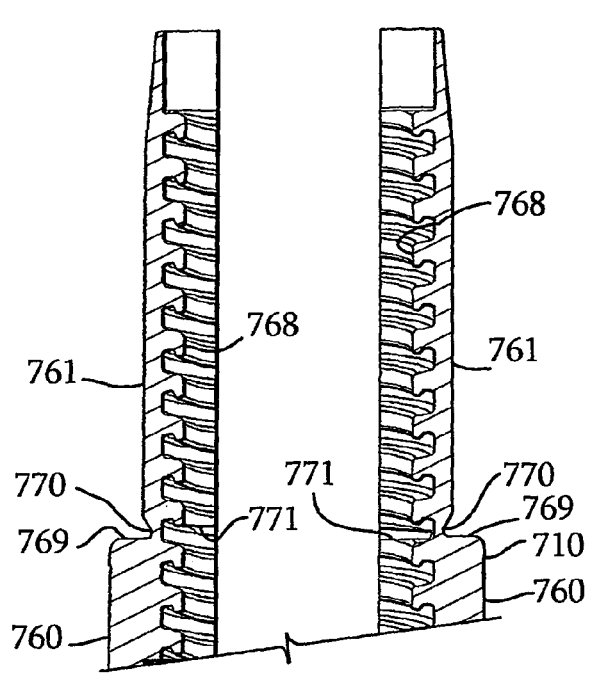
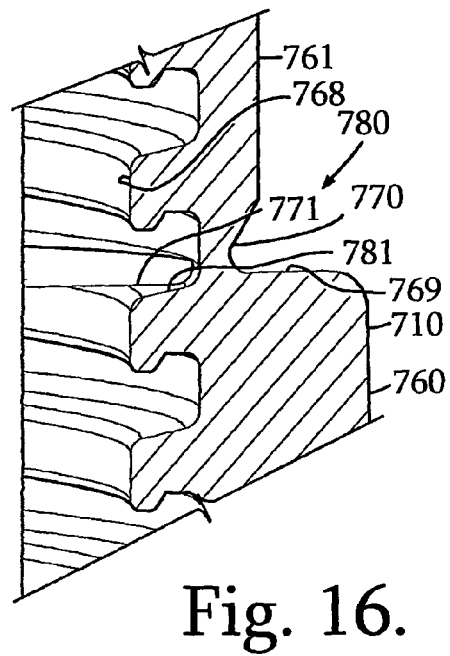
Fig. 16.
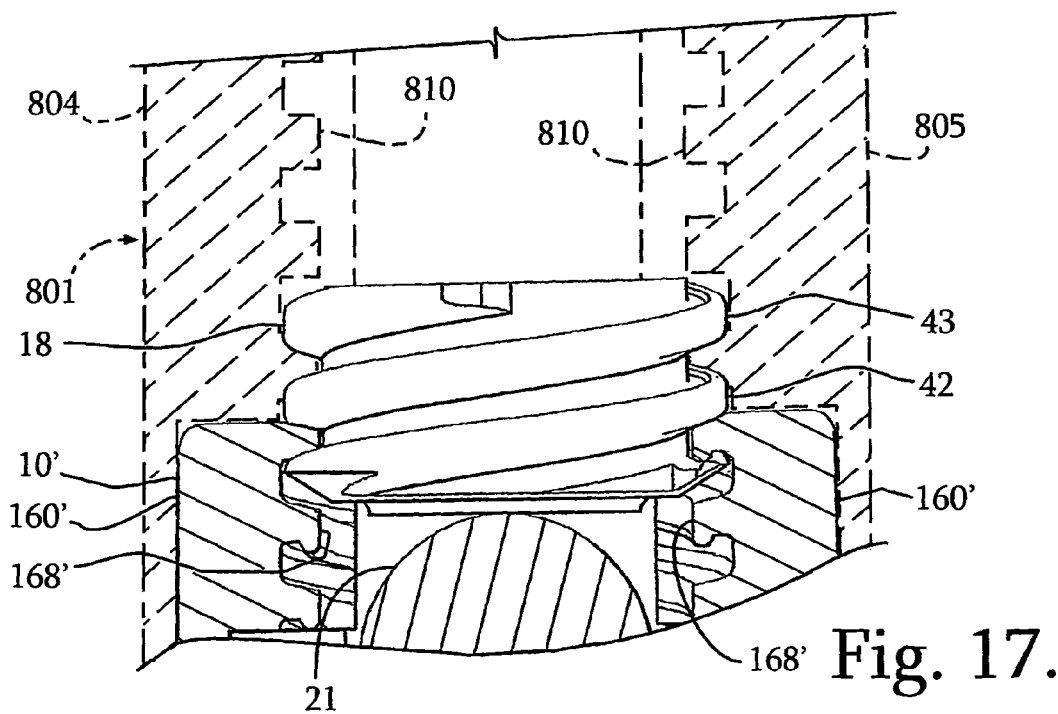
Fig. 17.

MULTI-START CLOSURES FOR OPEN IMPLANTS

CROSS-REFERENCE TO RELATED APPLICATIONS

This application claims the benefit of U.S. Provisional Patent Application Ser. No. 61/631,746 filed Jan. 10, 2012, that is incorporated by reference herein. This application also claims the benefit of U.S. Provisional Patent Application Ser. No. 61/634,361 filed Feb. 28, 2012, that is incorporated by reference herein.

BACKGROUND OF THE INVENTION

The present invention is directed to structure for joining together parts of a medical implant, in particular to closure mechanisms for use with open bone anchors in spinal surgery, and in some embodiments thereof, for use with spinal bone anchors such as polyaxial screws.

Bone anchors, such as bone screws and hooks are utilized in many types of spinal surgery in order to secure various implants to vertebrae along the spinal column for the purpose of stabilizing and/or adjusting spinal alignment. For example, the most common mechanism for providing vertebral support is to implant bone screws into certain bones which then in turn support a rod or are supported by the rod. Although both closed-ended and open-ended bone anchors are known, open-ended anchors are particularly well suited for connections to longitudinal connecting members such as hard, soft or deformable rods, dynamic or elastic connectors and connector arms, because such rods or other connector members do not need to be passed through a closed bore, but rather can be laid or urged into an open channel within a receiver or head of such a bone anchor. Generally, the anchors must be inserted into the bone as an integral unit or a preassembled unit, in the form of a shank or hook and connected pivotal receiver. In some instances, a portion of such a preassembled unit, such as a shank of a polyaxial bone screw assembly, may be independently implanted into bone, followed by push- or pop-on assembly of a receiver portion of the unit.

Typical open-ended bone screws include a threaded shank with a head or receiver having a pair of parallel projecting branches or arms which form a yoke with a U-shaped slot or channel to receive a rod or other longitudinal connecting member. Hooks and other types of connectors, as are used in spinal fixation techniques, may also include similar open ends for receiving rods or portions of other fixation and stabilization structure. The open-ended head or rod receiver portion of such implants typically includes a pair of spaced arms forming a channel closed by a closure member after the rod or other longitudinal connecting member is placed in the channel. Known closures include slide-on types, twist-on varieties that are rotated ninety degrees to a locked in position, and a variety of single start helically wound guide and advancement structures including, for example, thread forms having v-thread, reverse-angle buttress or square thread forms, to name a few, as well as other non-threadlike helically wound forms. Sometimes threaded plugs are utilized with outer threaded nuts to prevent splaying of the receiver arms.

As indicated above, the force required to press a closure structure down onto a rod or other connector located between arms of an open implant is considerable. Even though a head or receiver portion of an open polyaxial bone anchor may be pivoted in a direction to make it easier for the arms of the open implant to receive a rod or other connector, spinal misalignments, irregularities and the placement of other surgical tools make it difficult to place the rod or other connector between the arms of the implant while a closure structure is mated with the open implant as well as used to push the rod or other connector downwardly into the implant. For example, when the closure is a cylindrical plug having a single start helically wound guide and advancement structure, such structure must be aligned with mating structure on one of the implant arms and then rotated until a portion of the structure is captured by mating guide and advancement structure on both arms of the implant, all the while the closure is being pressed down on the rod while other forces are pushing and pulling the rod back out of the implant. Integral or mono-axial open implants that cannot be pivoted to receive the rod are even more difficult to manipulate during the initial placement of the rod and initial mating rotation of a closure plug between the spaced, open arms of the implant. Therefore, extraordinary forces are placed on the implant and closure plug while the surgeon either pushes down on the rod or pulls up on the bone to get the rod in position between the implant arms and to initially push down upon the rod with the closure plug.

SUMMARY OF THE INVENTION

A closure structure, top or plug of the invention for insertion between spaced arms of an open medical implant includes one or more helically wound guide and advancement features, each feature having a start surface or structure located at or near a bottom surface of the closure plug, each start structure simultaneously engaging and being captured by each of the spaced arms of the open implant upon initial rotation of the closure structure with respect to the open implant arms. According to an aspect of the invention, a double-start closure is disclosed having two helically wound forms thereon, each form having a start structure for simultaneously engaging a mating helical form on a respective open implant arm. Each time the illustrated duel- or double-start closure plug is rotated one turn (three hundred sixty degrees) between the implant arms, the closure plug advances axially into the implant and toward the rod by a width of two helical forms. The helically wound forms of the multi-start closure spiral around a cylindrical plug body thereof to an extent that the closure rotates over ninety degrees to fully or substantially receive the entire closure plug between the arms of the open implant. The illustrated closure is sized for at least one complete rotation (three hundred sixty degrees) of the plug with respect to the open implant to substantially receive the plug between the implant arms. Multi-start closures of the invention may have two or more coarse or fine helical forms, resulting in fewer or greater forms per axial distance spiraling about the closure plug body and thus resulting in plugs that rotate less (when more coarse) or more (when thin or fine) than one complete rotation to be fully received between the implant arms, typically, at least a ninety-one degree rotation is preferred.

An illustrated multi-start closure and mating open implant is in the form of non-threaded, interlocking flange forms. Also disclosed are multi-start closure structures provided with helically wound forms of other geometry, including, but not limited to helically wound threads such as reverse angle, buttress, square and v-threads. The multi-start closure may be cannulated for minimally invasive surgical applications.

Another illustrated multi-start closure embodiment of the invention is shown with a bone screw assembly having an open receiver with a pair of opposed arms, each arm having guide and advancement structure for simultaneous mating engagement with a start of the helically wound multi-start closure. A further embodiment according to the invention includes an open bone anchor receiver having integral upwardly extending break-off tabs that also have the guide and advancement structure for mating with the multi-start closure. A further embodiment includes an attachable/detachable guide tool cooperating with such a multi-start open receiver, the tool having inner guide and advancement structures located near a bottom thereof for rotatably and matingly receiving the multi-start closure and being synchronized with the receiver guide and advancement structure for rotating and driving the multi-start closure downward from the guide tool to the receiver.

Objects of the invention further include providing apparatus and methods that are easy to use and especially adapted for the intended use thereof and wherein the tools are comparatively inexpensive to produce. Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 9 is a front elevational view of an alternative closure of an embodiment of the invention, similar to the closure of FIG. 1, but including a break-off head, the alternative closure shown with a portion of a receiver of the polyaxial bone screw of FIG. 8 shown in enlarged and partial front elevation with portions broken away to show the detail thereof, and further showing a rod being pressed upon by the alternative closure, the rod also in partial front elevation with portions broken away to show the detail thereof.

FIG. 10 is another front elevational view of the closure of FIG. 9 with portions broken away to show the detail thereof.

FIG. 15 is a partial front elevational view of an embodiment of a multi-start open bone anchor receiver of an embodiment of the invention with portions broken away to show the detail thereof, the receiver including break-off tabs.

FIG. 16 is an enlarged and partial front elevational view of the receiver of FIG. 15 with portions broken away to show the detail thereof.

FIG. 17 is a partial front elevational view of an embodiment of a bone anchor receiver having a guide and advancement structure that matingly cooperates with the multi-start closure of FIG. 1, also shown in front elevation, the receiver having portions broken away to show the detail thereof, and further shown with a guide tool, shown in phantom, the guide tool having a multi-start guide and advancement structure receiving inner surface synchronized with the bone anchor receiver guide and advancement structure.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. It is also noted that any reference to the words top, bottom, up and down, and the like, in this application refers to the alignment shown in the various drawings, as well as the normal connotations applied to such devices, and is not intended to restrict positioning of the bone attachment structures in actual use.

Furthermore, the terms lead, pitch and start, as such terms are used to describe helically wound guide and advancement structures, are to be understood as follows: Lead is a distance along the axis of a closure plug that is covered by one complete rotation (360 degrees) of the closure plug with respect to a mating open implant. Pitch is the distance from a crest (or outer point or location) of one guide and advancement structure form to the next. For example in a single-start threadform, such as a single start, helically wound v-thread closure plug, lead and pitch are the same. Single start means that there is only one ridge or helically wound form wrapped around a cylindrical core, or in the case of the present invention, wrapped around a cylindrical closure plug body and thus there is only one start structure or surface at a base or forward end of the closure body that initially engages a mating structure on the open implant. Each time a single start closure rotates one turn (360 degrees), the closure has advanced axially by a width of one ridge or one helical form. Double-start means that there are two ridges or forms wrapped around a core body and thus there are two starting surfaces or structures on the closure plug. Therefore, each time a double-start body rotates one turn (360 degrees), such a body has advanced axially by a width of two ridges or forms. Multi-start means that there are at least two and may be up to three or more of such ridges or forms wrapped around a core body.

Figure 8:
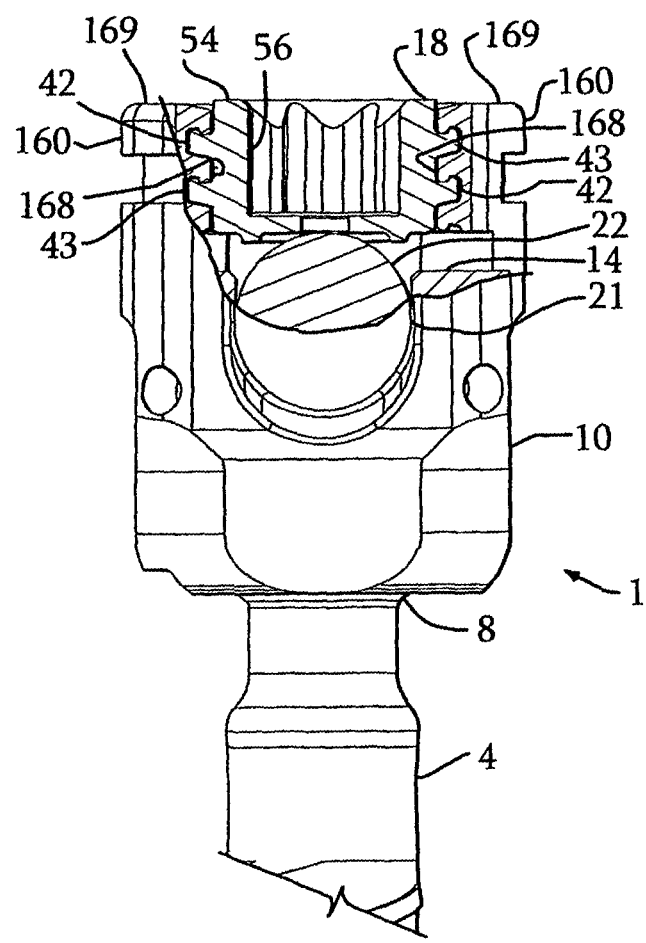
FIG. 8 a partial front elevational view of an open bone screw assembly, with portions broken away to show the detail thereof, including a receiver, a shank, a compression insert and also shown in engagement with the closure top of FIG. 1 (in reduced view) and a longitudinal connecting member in the form of a hard rod.

With reference to FIGS. 1-8, and in particular to FIG. 8, the reference number 1 generally represents an open implant in the form of a polyaxial bone screw apparatus or assembly that cooperates with an illustrated closure structure 18 embodiment of the invention. The bone screw assembly 1 is described in detail in U.S. Provisional Patent Application No. 61/631,746 filed Jan. 10, 2012 and incorporated by reference herein (hereafter the '746 application) and therefore will not be described in great detail herein. The description set forth in the '746 application includes a more detailed explanation of all the components referenced in FIG. 8. It is noted that multi-start closure embodiments of the invention, such as the closure 18 may be used with a variety of open implants including, but not limited to a wide variety of polyaxial screws, mono-axial or fixed screws, hooks and other types of open implants requiring a plug or closure mechanism to fix a rod or other implant member to a vertebra or other bone. Thus, the assembly 1 is only one example of how multi-start closures of the invention may be used.

Briefly, the illustrated assembly 1 includes a shank 4 with an upwardly extending upper portion or capture structure 8; an open receiver 10; a retaining structure or retainer (not shown) that pivots with the shank 4, a compression or pressure insert 14 and the multi-start closure structure or plug 18 in the form of a cylindrical plug having a double-start helically wound flange-form. The closure structure 18 presses against and captures a longitudinal connecting member, for example, a rod 21 which in turn engages the compression insert 14 that presses against the shank upper portion 8 that is attached to the retaining structure that in turn presses against an inner surface of the receiver 10, so as to capture and fix the longitudinal connecting member 21 within the receiver 10 and thus fix the member 21 relative to a vertebra (not shown). The illustrated receiver 10 and the shank 4 cooperate in such a manner that the receiver 10 and the shank 4 can be secured at any of a plurality of angles, articulations or rotational alignments relative to one another and within a selected range of angles both from side to side and from front to rear, to enable flexible or articulated engagement of the receiver 10 with the shank 4 until both are locked or fixed relative to each other near the end of an implantation procedure.

The illustrated rod 21 is hard, stiff, non-elastic and cylindrical, having an outer cylindrical surface 22. However, in other embodiments, the rod 21 may be elastic, deformable and/or of a different cross-sectional geometry. The rod 21 may be made from a variety of metals, metal alloys and deformable and less compressible plastics, including, but not limited to rods made of elastomeric, polyetheretherketone (PEEK) and other types of materials, such as polycarbonate urethanes (PCU) and polyethylenes. Furthermore, in lieu of a rod, longitudinal connecting members for use with the assembly 1 may take a variety of shapes, and/or may include a tensioned cord as described in greater detail in the '746 application that is incorporated by reference herein.

It is noted that the receiver 10 includes guide and advancement structures 168 that are shown as interlocking flange forms described in greater detail in applicant's U.S. Pat. No. 6,726,689, also incorporated by reference herein. Alternately, when the closure structure includes a different helical form, the receiver cooperating structures (e.g., 168) must also be of a cooperating, mating geometry, such as a square-shaped thread receiving form, a buttress thread receiving form, a reverse angle thread receiving form or other thread-like or non-thread-like helically wound discontinuous advancement structure receiving forms for operably guiding under rotation and advancing a multi-start closure structure downward between the receiver arms 160, as well as eventual torquing when the closure structure abuts against the rod 21 or other connecting member.

With particular reference to FIGS. 1-7, the illustrated multi-start closure structure 18 is a double start closure having a substantially cylindrical plug body 40 having an axis of rotation that is the same as that of the receiver 10 and including a helically wound guide and advancement structure in the form of a pair of helically wound forms 42 and 43, each illustrated as an interlocking flange form that operably joins with mating flange form guide and advancement structures 168 disposed on the arms of the receiver 10. The form 42 includes a start surface or structure 46 and the form 43 includes a start surface or structure 47. Each helically wound form 42 and 43 may take a variety of forms and geometries, including those described in Applicant's U.S. Pat. No. 6,726,689, which is incorporated by reference herein. It is noted (and also described in greater detail subsequently herein) that each of the closure structure guide and advancement structures or forms 42 and 43 could alternatively be in the form of a buttress thread, a square thread, a reverse angle thread, a v-thread or other thread like or non-thread like helically wound advancement structures, for operably guiding under rotation and advancing the closure structure downward between the arms of the receive 10 and preferably having such a nature as to resist splaying of the receiver arms when the closure structure 18 is advanced into the receiver channel. The specific flange forms 42 and 43 illustrated in FIGS. 1-7, as well as acceptable alternative locking forms, are described in detail in Applicant's U.S. Pat. No. 6,726,689, incorporated by reference herein, and thus shall not be discussed further herein. Such interlocking flange forms are preferred as the added strength provided thereby beneficially cooperate with and counter any reduction in strength caused by the any reduced profile of the receiver 10 that may more advantageously engage longitudinal connecting member components.

The illustrated closure structure 18 also includes a top surface 54 with an internal drive 56 in the form of an aperture that is illustrated as a star-shaped internal drive such as that sold under the trademark TORX, or may be, for example, a hex drive, or other internal drives such as slotted, tri-wing, spanner, two or more apertures of various shapes, and the like. A driving tool (not shown) sized and shaped for engagement with the internal drive 56 is used for both rotatable engagement and, if needed, disengagement of the closure 18 from the receiver 10 at arms 160. A base or bottom surface 58 of the closure is planar and further includes a rim 60 for engagement and penetration into the surface 22 of the rod 21 in certain embodiments of the invention. The closure top 18 further includes a cannulation through bore 62 extending along a central axis thereof and through a drive base surface 63 and the bottom surface 58 thereof. Such a through bore provides a passage through the closure 18 interior for a length of wire (not shown) inserted therein to provide a guide for insertion of the closure top into the receiver arms 160.

Figure 1:
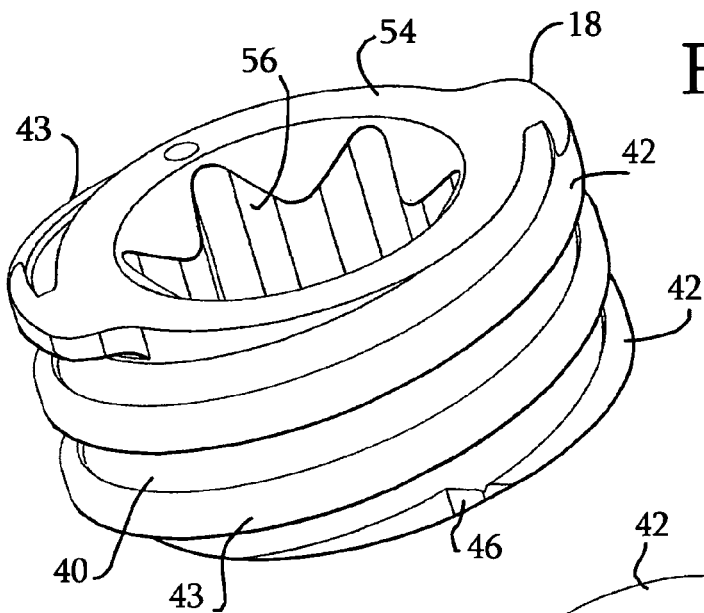
FIG. 1 is a perspective view of an embodiment of a multi-start closure according to the invention.
Figure 2:
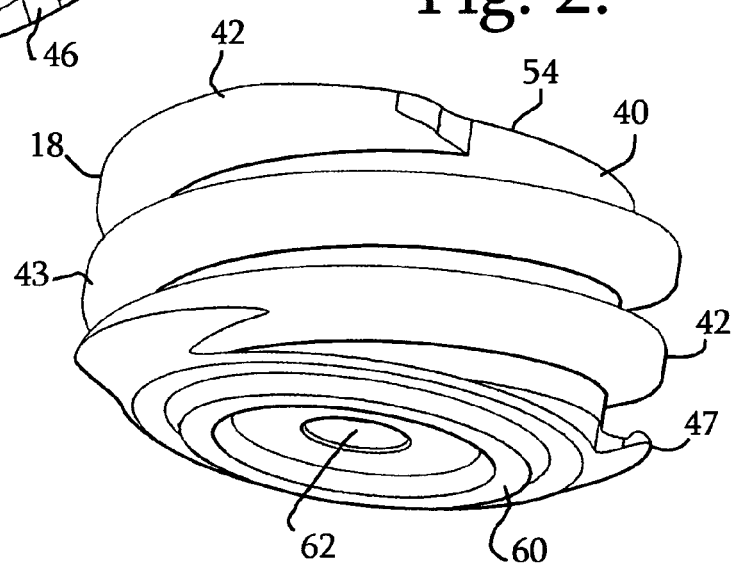
FIG. 2 is another perspective view of the multi-start closure of FIG. 1.
Figure 3:
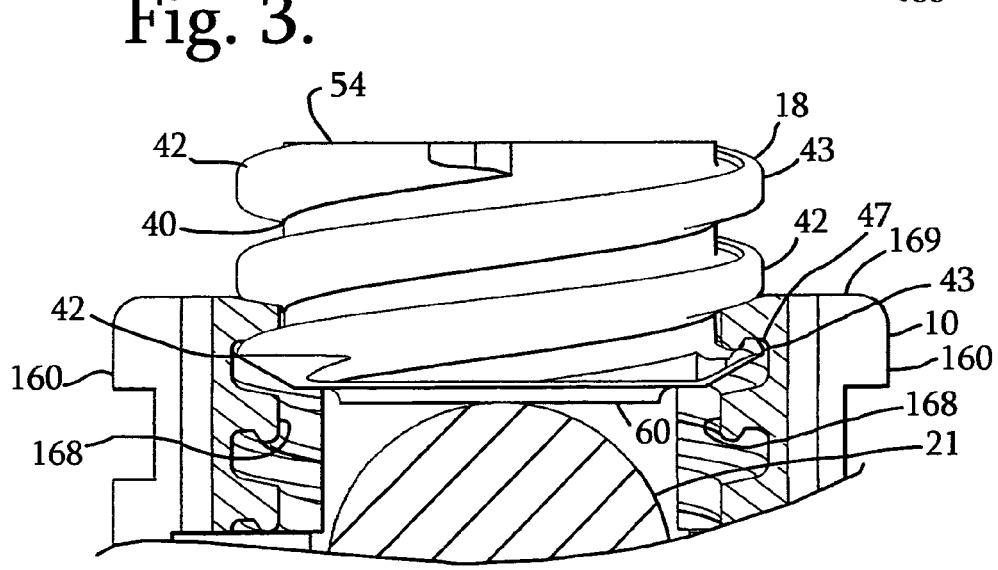
FIG. 3 is a front elevational view of the closure of FIG. 1 shown with a portion of a receiver of a polyaxial bone screw according to FIG. 8, the receiver shown in partial front elevation with portions broken away to show the detail thereof, and further showing a rod being pressed upon by the closure, the rod also in partial front elevation with portions broken away to show the detail thereof.
Figure 4:
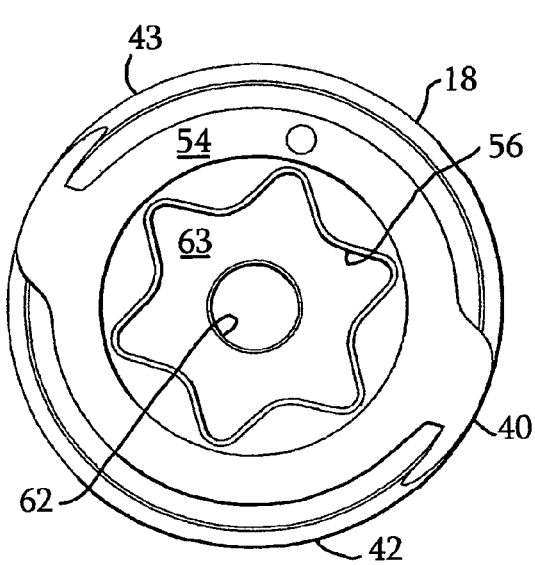
FIG. 4 is a reduced top plan view of the closure of FIG. 1.
Figure 5:
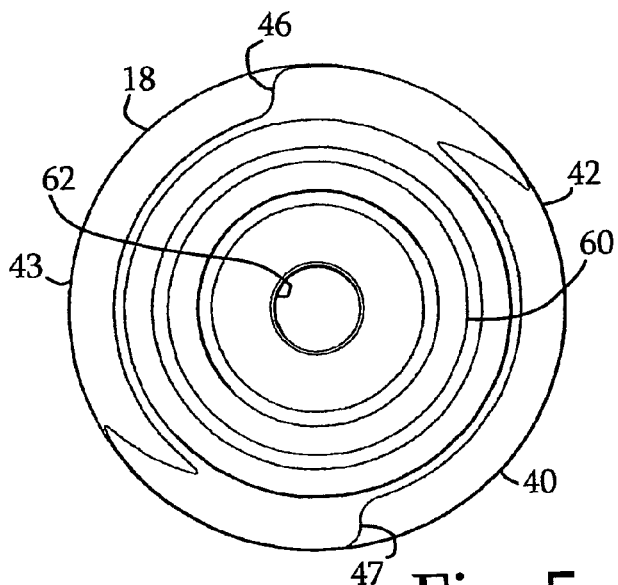
FIG. 5 is a reduced bottom plan view of the closure of FIG. 1.
Figure 6:
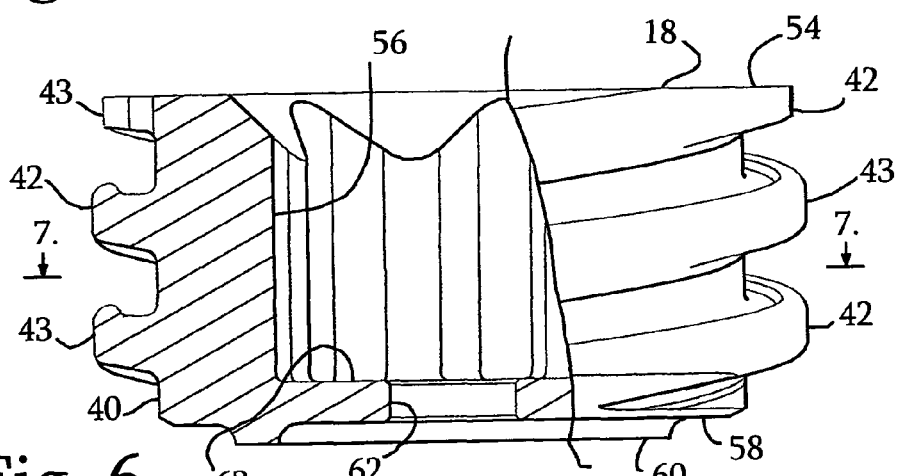
FIG. 6 is an enlarged front elevational view of the closure of FIG. 1 with portions broken away to show the detail thereof.
Figure 7:
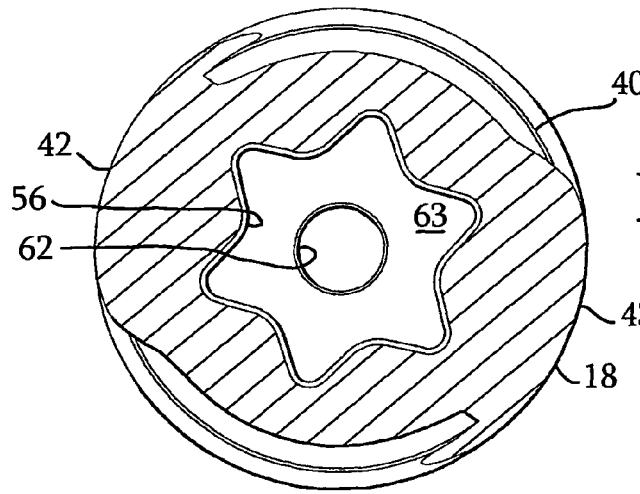
FIG. 7 is a reduced cross-sectional view taken along the line 7-7 of FIG. 6.

The closure structure 18 helically wound flange form start structures 46 and 47 of the respective forms 42 and 43 are located on opposite sides of the closure plug body 40 and are both located adjacent the bottom surface 58. As illustrated in FIG. 3, for example, when the closure structure 18 is rotated into the receiver 10 between receiver arms 160, each having a guide and advancement structure 168, the start 46 engages mating guide and advancement structure 168 on one arm 160 and the start 47 simultaneously engages guide and advancement structure 168 on the opposing arm 160, both forms 42 and 43 being simultaneously captured by the mating forms 168 on the opposed arms 160. As the structure 18 is rotated, the structure advances axially downwardly between the arms 160 and presses evenly down upon the captured rod 21. Each time the illustrated duel- or double-start closure plug 18 is rotated one complete turn or pass (three hundred sixty degrees) between the implant arms, the closure plug 18 advances axially into the implant and toward the rod by a width of two helical flange forms. The illustrated closure 18 is sized for at least one complete rotation (three hundred sixty degree) of the plug 18 with respect to the receiver 10 open arms 160 to substantially receive the plug between the implant arms. Multi-start closures of the invention may have two or more coarse or fine helical forms, resulting in fewer or greater forms per axial distance spiraling about the closure plug body and thus resulting in plugs that rotate less or more than one complete rotation to be fully received between the implant arms. Preferably, helically wound forms of the multi-start closure of the invention are sized so as to spiral around a cylindrical plug body thereof to an extent that the closure rotates at least ninety-one degrees to fully or substantially receive the closure plug between the arms of the bone screw receiver or other open implant. Particularly preferred guide and advancement structures are sized for at least one complete turn or pass (three-hundred sixty degree) of the closure between the receiver 10 arms and as many as two to three rotations to be fully received between implant arms.

In use, the receiver 10, the retainer 12 and the compression insert 14 are assembled with the shank 4 either before or after the shank is implanted into a vertebra, and the resulting assembly 1 is ultimately attached to the rod 21 or other longitudinal connecting member as described in the '746 application incorporated by reference herein. It is noted that the shank 4 and other bone screw assembly parts, the rod 21 (also having a central lumen in some embodiments) and the closure top 18 having the central bore 62 can be inserted in a percutaneous or minimally invasive surgical manner, utilizing guide wires. After the rod 21 or other longitudinal connecting member is positioned in an open or percutaneous manner in cooperation with the at least two bone screw assemblies 1 (or other open implants), the closure structure 18 is then inserted into and advanced between the arms 160 of each of the receiver 10. The closure structure 18 is rotated, using a tool engaged with the inner drive 56 until a selected pressure is reached at which point the rod 21 engages a U-shaped seating surface of the compression insert 14, further pressing the insert against the shank upper portion 8 and attached retainer into locked frictional engagement with the receiver 10. Prior to locking the insert 14 against the shank head 8, the shank 4 may be pivoted to a plurality of potentially desirable positions with respect to the receiver 10, followed by locking of the polyaxial mechanism by fully mating the multi-start closure top 18 with the receiver 10. Different angular or articulated positions of the shank 4 with respect to the receiver 10 are shown in the '746 application incorporated by reference herein.

With specific reference to FIGS. 3 and 8, as the multi-start closure structure 18 rotates and moves downwardly into the respective receiver 10, the rim 60 engages and penetrates the rod surface 22, the closure structure 18 pressing downwardly against and biasing the rod 21 into compressive engagement with the insert 14 that urges the shank upper portion 8 and attached retainer into locking engagement with the receiver, the retainer outer surface frictionally abutting an inner spherical seating surface of the receiver 10. For example, about 80 to about 120 inch pounds of torque on the closure top may be applied for fixing the bone screw shank 6 with respect to the receiver 10. Also, for example, when the shank 4 is disposed at an angle with respect to the receiver 10, a part of the shank upper portion 8 may also be in frictional engagement with a portion of the receiver spherical seating surface.

If removal of the rod 21 from any of the bone screw assemblies 1 is necessary, or if it is desired to release the rod 21 at a particular location, disassembly is accomplished by using the driving tool (not shown) that mates with the internal drive 56 on the closure structure 18 to rotate and remove such closure structure from the cooperating receiver 10. Disassembly is then accomplished in reverse order to the procedure described previously herein for assembly.

With reference to FIGS. 9 and 10, an alternative closure top 18' is shown that is almost identical to the closure top 18. However, the top 18' differs from the top 18 in that the top 18' includes a break-off head 70' that further includes a top surface 72' having tooling notches 73', an outer faceted driving surface 74', illustrated as having a hex-shaped profile, and an inner bore 76'. Otherwise, the closure top 18' includes a body 40', a first helical form 42', a second helical form 43', a body top surface 54', a body internal drive 56', a base 58', a rim 60', a cannulation bore 62' and a drive base surface 63' that is the same or substantially similar to the respective body 40, first helical form 42, second helical form 43, body top surface 54, internal drive 56, base 58, rim 60, cannulation bore 62 and drive base surface 63 previously described herein with respect to the closure top 18. The break-off head 70' is integral with the body 40' at the body top surface 54'. The inner bore 76' communicates with the inner drive 56' and the cannulation bore 62'. The break-off head 70' is designed to allow such head 70' to break from the body 40' at or near the top surface 54' at a preselected torque, for example, 70 to 140 inch pounds, when a hex-shaped tool (not shown) engages the outer surfaces 74' and drives the closure structure 18' into the receiver 10 as shown in FIG. 9. The inner drive 56' is used for disassembly or loosening of the closure 18' from the receiver 10, and re-tightening, if needed.

Figure 11:
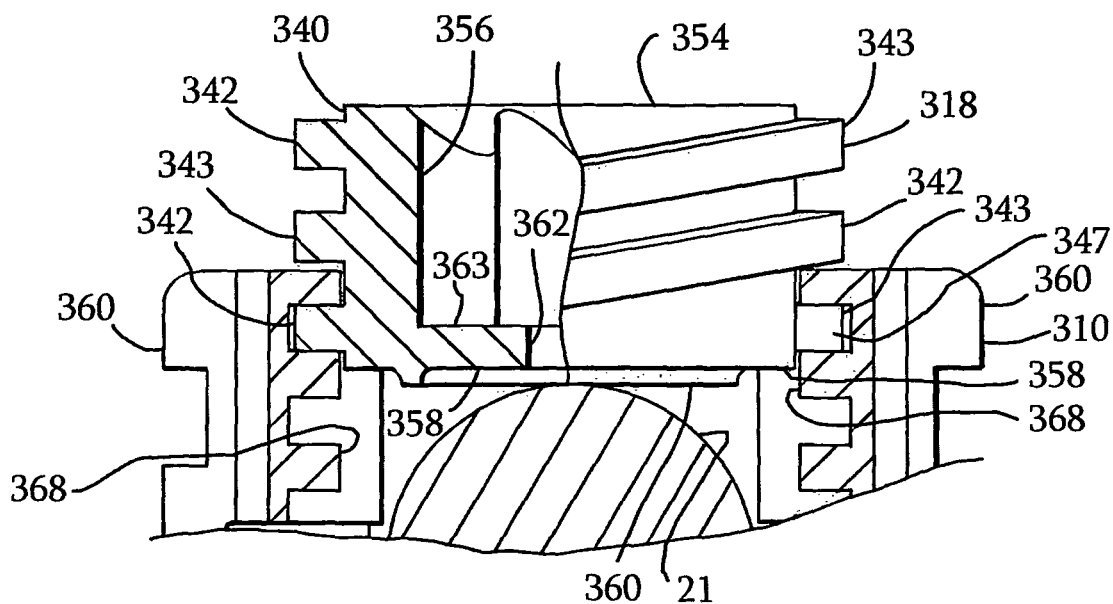
FIG. 11 is a front elevational view of an alternative square-thread closure of an embodiment of the invention with portions broken away to show the detail thereof, the closure shown with a portion of a receiver of the polyaxial bone screw of FIG. 8 shown in enlarged and partial front elevation with portions broken away to show the detail thereof, and further showing a rod being pressed upon by the alternative closure, the rod also in partial front elevation with portions broken away to show the detail thereof.

With reference to FIG. 11, another alternative multi-start closure top 318 is shown that is almost identical to the closure top 18 with the exception that the two flange forms 42 and 43 with respective starts 46 and 47 have been replaced with square threads 342 and 343 with respective starts 346 (not shown) and 347. Otherwise, the dual or double start closure top 318 includes a body 340, a body top surface 354, a body internal drive 356, a base 358, a rim 360', a cannulation bore 362 and a drive base surface 363 that is the same or substantially similar to the respective body 40, body top surface 54, internal drive 56, base 58, rim 60, cannulation bore 62 and drive base surface 63 previously described herein with respect to the closure top 18. In FIG. 11, the closure top 318 is shown partially wound into a polyaxial bone screw receiver 310 having opposed arms 360 with inner surfaces equipped with guide and advancement structures 368 that are sized and shaped to simultaneously closely receive and mate with the square threads 342 and 343 of the double closure structure 318. Otherwise, the receiver 310 is identical or substantially similar to the receiver 10 described in detail in the '746 application incorporated by reference herein.

Figure 12:
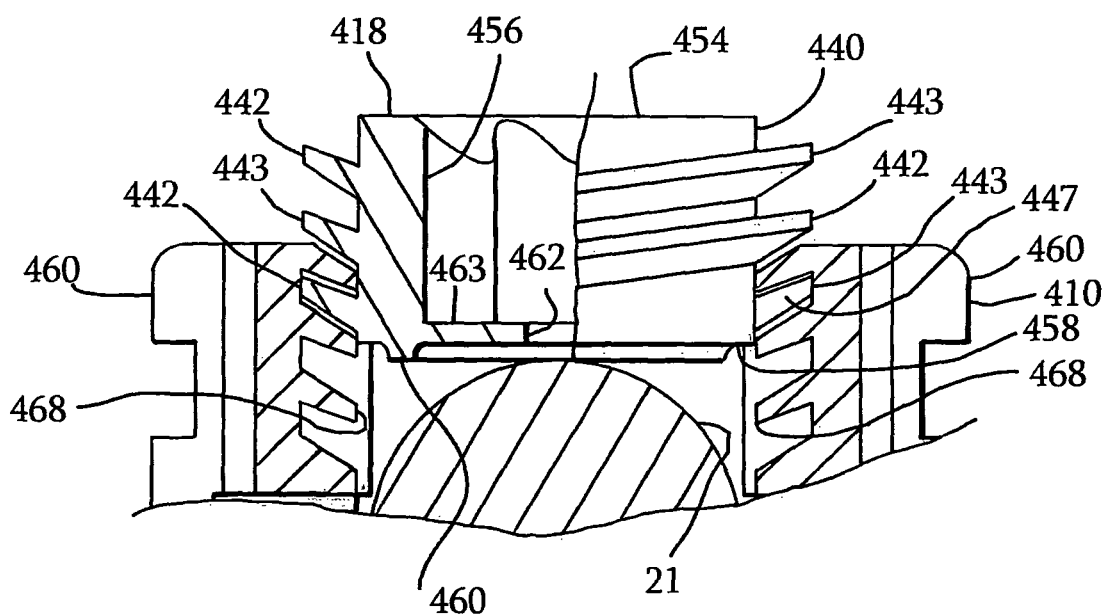
FIG. 12 is a front elevational view of an alternative reverse angle closure of an embodiment of the invention with portions broken away to show the detail thereof, the closure shown with a portion of a receiver of the polyaxial bone screw of FIG. 8 shown in enlarged and partial front elevation with portions broken away to show the detail thereof, and further showing a rod being pressed upon by the alternative closure, the rod also in partial front elevation with portions broken away to show the detail thereof.

With reference to FIG. 12, an alternative multi-start closure top 418 is shown that is almost identical to the closure top 18 with the exception that the two flange forms 42 and 43 with respective starts 46 and 47 have been replaced with reverse angle threads 442 and 443 with respective starts 446 (not shown) and 447. Otherwise, the dual or double start closure top 418 includes a body 440, a body top surface 454, a body internal drive 456, a base 458, a rim 460', a cannulation bore 462 and a drive base surface 463 that is the same or substantially similar to the respective body 40, body top surface 54, internal drive 56, base 58, rim 60, cannulation bore 62 and drive base surface 63 previously described herein with respect to the closure top 18. The closure top 418 is shown partially wound into a polyaxial bone screw receiver 410 having opposed arms 460 with inner surfaces equipped with guide and advancement structures 468 that are sized and shaped to simultaneously closely receive and mate with the reverse angle threads 442 and 443 of the double start closure structure 418. Otherwise, the receiver 410 is identical or substantially similar to the receiver 10 described in detail in the '746 application incorporated by reference herein.

Figure 13:
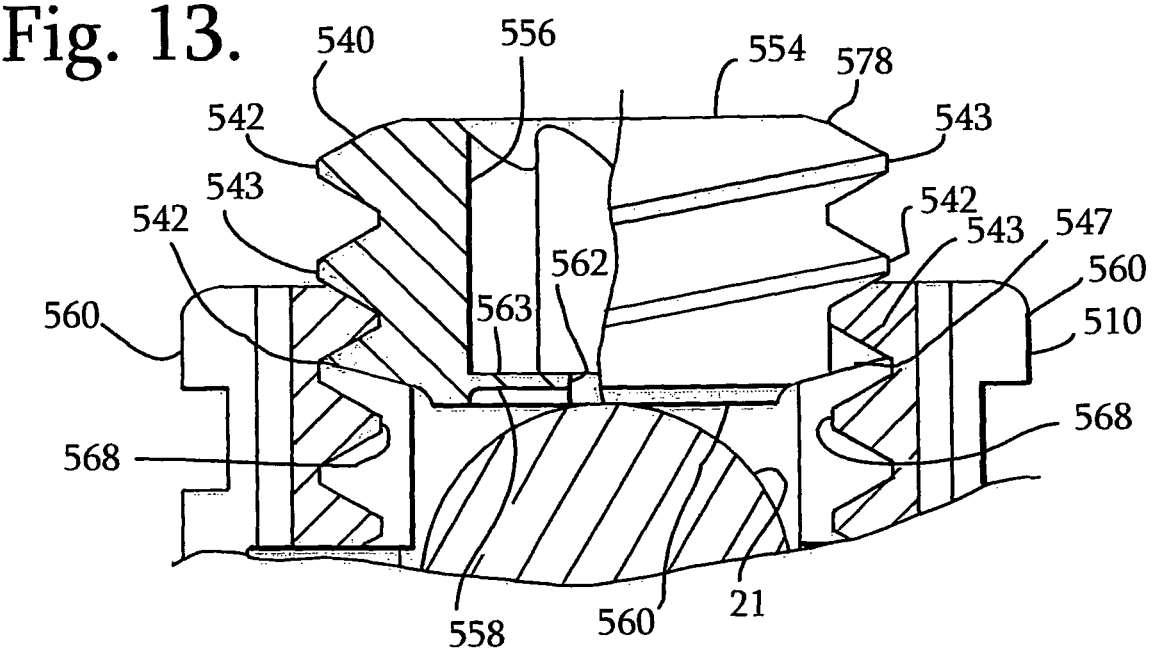
FIG. 13 is a front elevational view of an alternative v-thread closure embodiment of the invention with portions broken away to show the detail thereof, the closure shown with a portion of a receiver of the polyaxial bone screw of FIG. 8 shown in enlarged and partial front elevation with portions broken away to show the detail thereof, and further showing a rod being pressed upon by the alternative closure, the rod also in partial front elevation with portions broken away to show the detail thereof.

With reference to FIG. 13, another alternative multi-start closure top 518 is shown that is almost identical to the closure top 18 with the exception that the two flange forms 42 and 43 with respective starts 46 and 47 have been replaced with v-threads 542 and 543 with respective starts 546 (not shown) and 547. Otherwise, the dual or double start closure top 518 includes a body 540, a body top surface 554, a body internal drive 556, a base 558, a rim 560', a cannulation bore 562 and a drive base surface 563 that is the same or substantially similar to the respective body 40, body top surface 54, internal drive 56, base 58, rim 60, cannulation bore 62 and drive base surface 63 previously described herein with respect to the closure top 18. The closure top 518 is shown partially wound into a polyaxial bone screw receiver 510 having opposed arms 560 with inner surfaces equipped with guide and advancement structures 568 that are sized and shaped to simultaneously closely receive and mate with the threads 542 and 543 of the double start closure structure 518. Otherwise, the receiver 510 is identical or substantially similar to the receiver 10 described in detail in the '746 application incorporated by reference herein.

Figure 14:
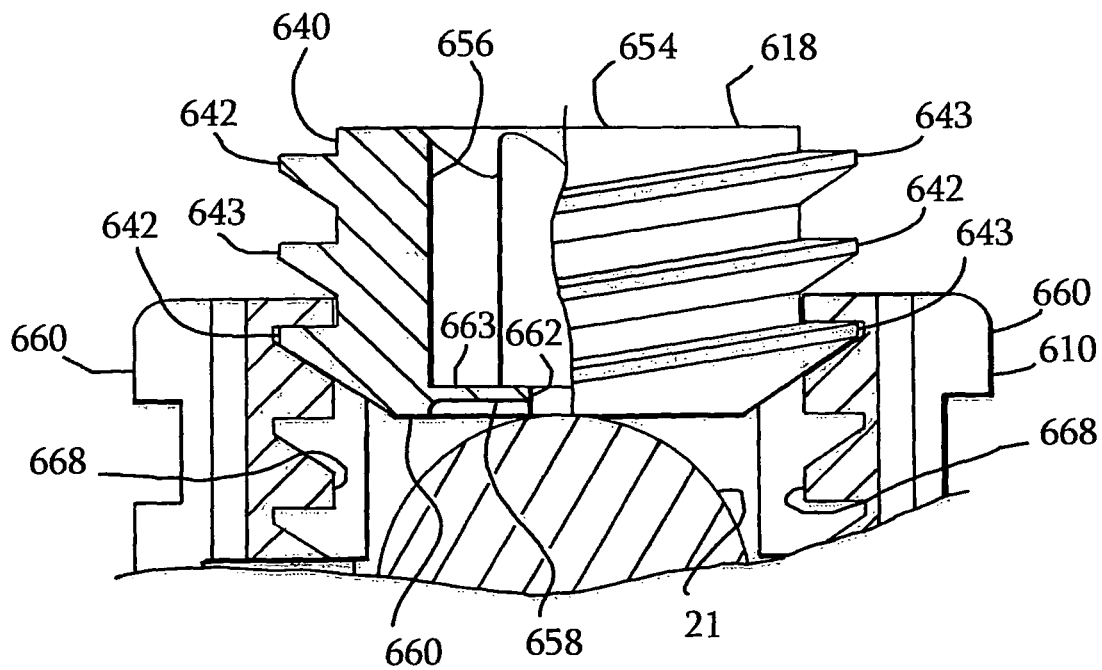
FIG. 14 is a front elevational view of an alternative buttress-thread closure embodiment of the invention with portions broken away to show the detail thereof, the closure shown with a portion of a receiver of the polyaxial bone screw of FIG. 8 shown in enlarged and partial front elevation with portions broken away to show the detail thereof, and further showing a rod being pressed upon by the alternative closure, the rod also in partial front elevation with portions broken away to show the detail thereof.

With reference to FIG. 14, another alternative multi-start closure top 618 is shown that is almost identical to the closure top 18 with the exception that the two flange forms 42 and 43 with respective starts 46 and 47 have been replaced with buttress threads 642 and 643 with respective starts 446 and 447 (not shown). Otherwise, the dual or double start closure top 618 includes a body 640, a body top surface 654, a body internal drive 656, a base 658, a rim 660', a cannulation bore 662 and a drive base surface 663 that is the same or substantially similar to the respective body 40, body top surface 54, internal drive 56, base 58, rim 60, cannulation bore 62 and drive base surface 63 previously described herein with respect to the closure top 18. The closure top 618 is shown partially wound into a polyaxial bone screw receiver 610 having opposed arms 660 with inner surfaces equipped with guide and advancement structures 668 that are sized and shaped to simultaneously closely receive and mate with the buttress threads 642 and 643 of the double start closure structure 618. Otherwise, the receiver 610 is identical or substantially similar to the receiver 10 described in detail in the '746 application incorporated by reference herein.

With reference to FIGS. 15 and 16, an open receiver 710 is illustrated that is substantially similar to the receiver 10 previously described herein with the exception that the receiver 710 includes opposed arms 760, each having an integral upstanding break-off extension 761. Each receiver arm 760 and integral extension 761 has an inner helically wound guide and advancement structure 768 that is sized and shaped to mate with the flange forms 42 and 43 of the dual start closure 18 previously described herein. The break-off extensions 761 are initially integral with the respective arms 760 and are then broken off by a user after the closure 18 has been rotatingly advanced along the arm extensions 761 and into the channel located between the receiver arms 760. In the illustrated embodiment, in addition to an outer groove or notch 770 located at or near a top surface 769 of each of the arms 760 where the extensions 761 break off from the receiver arms, illustrated inner arm surfaces include a recess or cut 771, best shown in FIG. 16, that runs substantially horizontally. Each recess 771 is curved and elongate and disposed somewhat cross-wise or transverse to the respective flange form 768. For example, with reference to the arm 760 shown in FIG. 16, the recess 771 cuts into a weakened region, generally, 780, where the arm 760 joins with the respective attached adjacent extension 761, the curved and elongate recess 771 beginning at a lower portion or location 781 of the flange form recess or segment and terminating at an opposed upper end location of the flange form segment, while otherwise leaving the flange form 768 intact. Stated in another way, the substantially horizontally extending recess 771 cuts into both a lead portion and a trailing portion of each of the flange form segments located near and directly above the opposed arms 760 and substantially opposite the notch 770, thus further weakening the region where the extension and the arm attach, without destroying the flange form path, so that the closure 18 is not derailed by the recess 771 or otherwise prohibited from moving downwardly into the receiver channel formed between the receiver arms 760.

With reference to FIG. 17, the multi-start closure 18 is shown cooperating with a spinal implant receiver, such as a bone screw receiver 10' and a discrete, detachable guide tool 801. The elongate guide tool 801, only partially shown in FIG. 17, is typically sized for extending from the bone screw receiver 10' upwardly to a location outside of a patient, the tool providing a guide channel for operably guiding the rod 21 or other longitudinal connecting member from a position exterior of the bone screw receiver 10' toward and into the bone screw receiver 10'. The illustrated guide tool has opposed arms 805, each arm having a helical guide and advancement structure 810 thereon that is illustrated as a square thread form, but may be of other geometry, including a flange form the same or similar to the flange forms 168' of the receiver 10' that mates with the flange forms 42 and 43 of the closure structure 18. Thus, the illustrated structures 810 are sized and shaped for receiving and rotating engagement with a dual start closure. The closure 18 is shown partially wound into the receiver 10' that is identical or substantially similar to the receiver 10 with the exception of certain outer arm surface features (not shown). Thus, the receiver 10' includes opposed arms 160' with inner surfaces having guide and advancement structures 168' that are sized and shaped to simultaneously closely receive and mate with the flange forms 42 and 43 of the dual start closure structure 18. The guide tool 801 includes attachment structure for detachable attachment to the receiver 10'(not shown), that may take a variety of forms and methods, including, but not limited to a slide-on, slide-off attachment, a snap-on, rotate off attachment, a rotate-on and rotate-off attachment, to name a few. For example, cooperating attachment structure for both the tool and the receiver may be used that is disclosed in U.S. Pat. No. 7,470,279 and incorporated by reference herein. Returning to the inner helically wound guide and advancement structure 810 formed on each arm 804 of the guide tool 801, the structure 810 is sized and shaped for being aligned with the receiver arms 160' during removable attachment of the tool 801 with the respective bone screw receiver 10' so as to continue the helical pathway for the closure 18, the structures 810 being synchronized with the flange forms 168' to allow for the rotation and driving transfer of the closure 18 from the tool 801 into the receiver 10'.

It is to be understood that while certain forms of the present invention have been illustrated and described herein, it is not to be limited to the specific forms or arrangement of parts described and shown.

The invention claimed is:

1. In a medical implant having a substantially cylindrical closure member and a receiver member having first and second spaced arms forming an open channel, the closure member having an axis of rotation for closing the open channel, the improvement comprising:
   a) first and second helically wound forms located on the closure member, the first form having a first start and the second form having a second start; and
   b) a first discontinuous helically wound structure on the receiver first arm and a second discontinuous helically wound structure on the receiver second arm and wherein simultaneous mating of the first start with the arm first helically wound structure and the second start with the arm second helically wound structure occurs when the closure member is rotated between the first and second arms of the receiver member.

2. The improvement of claim 1 wherein the first and second helically wound forms are each a flange form that interlocks with the respective helically wound structures on the receiver.

3. The improvement of claim 1 wherein the first and second helically wound forms are v-threads.

4. The improvement of claim 1 wherein the first and second helically wound forms are square threads.

5. The improvement of claim 1 wherein the first and second helically wound forms are reverse angle threads.

6. The improvement of claim 1 wherein the first and second helically wound forms are buttress threads.

7. The improvement of claim 1 wherein the closure member has a break-off head.

8. The improvement of claim 1 wherein the receiver has break-off extensions.

9. The improvement of claim 1 further comprising a guide tool having third and fourth arms detachably attached to the receiver, the guide tool having a third discontinuous helically wound structure on the guide tool third arm and a fourth discontinuous helically wound structure on the guide tool fourth arm and wherein simultaneous mating of the first start with the third helically wound structure and the second start with the fourth helically wound structure occurs when the closure member is rotated between the third and fourth arms of the guide tool, the guide tool third and fourth helically wound structures sized and shaped to provide transfer of the closure member between the guide tool and the bone screw upon rotation of the closure.

10. A medical implant comprising:
   a) a receiver having a body and a pair of upstanding spaced arms forming a channel for receiving a longitudinal connecting member, each arm having an inwardly facing surface with a first discontinuous helically wound guide and advancement structure located thereon; and
   b) a closure structure having a cylindrical body and a second helically wound guide and advancement structure having at least two starts.

11. The implant of claim 10 wherein the first and second helically wound guide and advancement structures are interlocking flange forms.

12. The improvement of claim 10 wherein the second helically wound guide and advancement structure includes at least two v-threads.

13. The improvement of claim 10 wherein the second helically wound guide and advancement structure includes at least two square threads.

14. The improvement of claim 10 wherein the second helically wound guide and advancement structure includes at least two reverse angle threads.

15. The improvement of claim 10 wherein the second helically wound guide and advancement structure includes at least two buttress threads.

16. The improvement of claim 10 wherein the closure structure has a break-off head.

17. The improvement of claim 10, wherein the receiver has break-off extensions.

18. In a medical implant, the improvement comprising:
   a) an open receiver member with spaced arms having inwardly facing surfaces, each with a helically wound guide and advancement form located thereon; and
   b) a helically wound multi-start closure member having an axis of rotation, the closure member rotatably mounted on the receiver member at the spaced arm inwardly facing surfaces.

19. The improvement of claim 18 wherein the multi-start closure is a double-start closure.

20. The improvement of claim 18 wherein the multi-start closure includes at least two helically wound forms, each form being one of a flange form, a v-thread, a square thread, a reverse angle thread and a buttress thread, the form mating with the first helically wound guide and advancement form.

21. In a polyaxial bone anchor having a shank and a receiver, the shank being pivotable with respect to the receiver prior to locking of a position of the shank with respect to the receiver, the improvement wherein:
   a) the receiver has spaced arms having inwardly facing surfaces, each surface having a helically wound guide and advancement form located thereon, each guide and advancement form being sized and shaped to mate with a helically wound multi-start closure member having at least two starts.

22. The improvement of claim 21 further comprising an attachable and detachable guide tool cooperating with the receiver, the guide tool having at least two arms, each arm having helically wound guide and advancement structure thereon in synchronized relationship with the receiver helically wound guide and advancement forms to provide transfer of the multi-start closure member between the guide tool and the bone anchor upon rotation of the closure.

* * * * *